US012396810B2

(12) United States Patent
Tsao et al.

(10) Patent No.: US 12,396,810 B2
(45) Date of Patent: Aug. 26, 2025

(54) SYSTEM AND METHOD FOR AUTOMATED IMAGE-GUIDED ROBOTIC INTRAOCULAR SURGERY

(71) Applicant: THE REGENTS OF THE UNIVERSITY OF CALIFORNIA, Oakland, CA (US)

(72) Inventors: Tsu-Chin Tsao, Los Angeles, CA (US); Jean-Pierre Hubschman, Los Angeles, CA (US); Cheng-Wei Chen, Los Angeles, CA (US); Yu-Hsiu Lee, Los Angeles, CA (US); Matthew Gerber, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 1051 days.

(21) Appl. No.: 17/052,758

(22) PCT Filed: May 14, 2019

(86) PCT No.: PCT/US2019/032236
§ 371 (c)(1),
(2) Date: Nov. 3, 2020

(87) PCT Pub. No.: WO2019/222228
PCT Pub. Date: Nov. 21, 2019

(65) Prior Publication Data
US 2021/0228292 A1   Jul. 29, 2021

Related U.S. Application Data

(60) Provisional application No. 62/671,928, filed on May 15, 2018.

(51) Int. Cl.
*A61B 34/32* (2016.01)
*A61B 34/10* (2016.01)
(Continued)

(52) U.S. Cl.
CPC .............. *A61B 34/32* (2016.02); *A61B 34/10* (2016.02); *A61F 9/00736* (2013.01); *A61B 3/14* (2013.01);
(Continued)

(58) Field of Classification Search
CPC .......... A61B 34/32; A61B 34/10; A61B 3/14; A61B 2034/107; A61B 2090/3735;
(Continued)

(56) References Cited

U.S. PATENT DOCUMENTS 4,943,296 A   7/1990 Funakubo et al.
5,312,396 A   5/1994 Feld et al.
(Continued)

FOREIGN PATENT DOCUMENTS

AU   2019347754 A1   4/2021
BR   112021010641 A2   9/2021
(Continued)

OTHER PUBLICATIONS

Yu et al., Calibration and Integration of B-Mode Optical Coherence Tomography for Assistive Control in Robotic Microsurgery, in IEEE/ASME Transactions on Mechatronics, vol. 21, No. 6, pp. 2613-2623, Dec. 2016, doi: 10.1109/TMECH.2016.2583259.*
(Continued)

*Primary Examiner* — Bo Joseph Peng
(74) *Attorney, Agent, or Firm* — Foley & Lardner LLP

(57) ABSTRACT

A surgical system includes: (1) an imaging device configured to acquire imaging data of a surgical site; (2) a surgical manipulator configured to hold a surgical tool; and (3) a controller connected to the imaging device and the surgical manipulator, wherein the controller is configured to receive the imaging data from the imaging device and derive, from the imaging data, an insertion trajectory for the surgical tool through an incision at the surgical site.

19 Claims, 18 Drawing Sheets

(51) Int. Cl.
  *A61F 9/007* (2006.01)
  *A61B 3/14* (2006.01)
  *A61B 90/00* (2016.01)
(52) U.S. Cl.
  CPC . *A61B 2034/107* (2016.02); *A61B 2090/3735* (2016.02)
(58) Field of Classification Search
  CPC ..... A61B 90/11; A61B 90/14; A61F 9/00736; A61F 9/00825; A61F 2009/00851; A61F 2009/0087; A61F 2009/00887
  See application file for complete search history.

(56) References Cited

U.S. PATENT DOCUMENTS

| | | | |
|---|---|---|---|
| 8,348,861 B2 | 1/2013 | Glozman et al. | |
| 8,886,330 B2 | 11/2014 | Taylor et al. | |
| 8,911,429 B2 | 12/2014 | Olds et al. | |
| 9,020,613 B2 | 4/2015 | Taylor et al. | |
| 9,125,556 B2 | 9/2015 | Zehavi et al. | |
| 9,445,946 B2 | 9/2016 | Angeley et al. | |
| 9,554,864 B2 | 1/2017 | Taylor et al. | |
| 9,662,174 B2 | 5/2017 | Taylor et al. | |
| 9,743,996 B2 | 8/2017 | Neubach et al. | |
| 9,770,828 B2 | 9/2017 | Taylor et al. | |
| 9,815,206 B2 | 11/2017 | Balicki et al. | |
| 9,849,029 B2 | 12/2017 | Ammari et al. | |
| 9,993,313 B2 | 6/2018 | Schuh et al. | |
| 10,145,747 B1 | 12/2018 | Lin et al. | |
| 10,166,080 B2 | 1/2019 | Balicki et al. | |
| 10,188,552 B2 | 1/2019 | He et al. | |
| 10,226,304 B2 | 3/2019 | Iordachita et al. | |
| 10,406,026 B2 | 9/2019 | Simaan et al. | |
| 10,617,561 B2 | 4/2020 | Meenink | |
| 10,667,871 B2 | 6/2020 | Romo et al. | |
| 10,687,784 B2 | 6/2020 | Shoham | |
| 10,744,035 B2 | 8/2020 | Alvarez et al. | |
| 10,820,954 B2 | 11/2020 | Marsot et al. | |
| 10,888,384 B2 | 1/2021 | Rosielle et al. | |
| 10,888,389 B2 | 1/2021 | Draelos et al. | |
| 11,013,565 B2 | 5/2021 | Beelen et al. | |
| 11,197,720 B2 | 12/2021 | Zarrouk et al. | |
| 12,016,740 B2 | 6/2024 | Gerber et al. | |
| 12,239,398 B2 | 3/2025 | Beelen et al. | |
| 2003/0013949 A1* | 1/2003 | Moll ................ | G09B 23/285 600/407 |
| 2011/0202070 A1 | 8/2011 | Dario et al. | |
| 2011/0282190 A1* | 11/2011 | Caffey ............... | A61B 5/0066 600/427 |
| 2012/0226145 A1 | 9/2012 | Chang et al. | |
| 2012/0310042 A1 | 12/2012 | Joos et al. | |
| 2013/0079711 A1 | 3/2013 | Nair et al. | |
| 2013/0123798 A1 | 5/2013 | Tsao et al. | |
| 2013/0338679 A1 | 12/2013 | Rosielle et al. | |
| 2014/0142591 A1 | 5/2014 | Alvarez et al. | |
| 2015/0018840 A1 | 1/2015 | Monfaredi et al. | |
| 2015/0245875 A1 | 9/2015 | Meenink | |
| 2015/0297177 A1 | 10/2015 | Boctor et al. | |
| 2015/0342695 A1 | 12/2015 | He et al. | |
| 2017/0000567 A1 | 1/2017 | Kim et al. | |
| 2017/0172698 A1 | 6/2017 | Charles | |
| 2017/0354387 A1 | 12/2017 | McCarthy | |
| 2018/0018953 A1 | 1/2018 | Todd et al. | |
| 2018/0185113 A1* | 7/2018 | Gregerson ............ | A61B 34/30 |
| 2019/0099226 A1 | 4/2019 | Hallen | |
| 2019/0206565 A1 | 7/2019 | Shelton | |
| 2019/0223974 A1 | 7/2019 | Romo et al. | |
| 2019/0290109 A1 | 9/2019 | Agrawal et al. | |
| 2019/0374383 A1 | 12/2019 | Alvarez et al. | |
| 2020/0029948 A1 | 1/2020 | Wong et al. | |
| 2020/0155232 A1 | 5/2020 | Wong | |
| 2020/0352782 A1 | 11/2020 | Bach et al. | |
| 2021/0007778 A1 | 1/2021 | Shoham | |
| 2021/0153962 A1 | 5/2021 | Naus et al. | |
| 2021/0161712 A1 | 6/2021 | Schaller et al. | |
| 2021/0220067 A1 | 7/2021 | Charles | |
| 2022/0022981 A1 | 1/2022 | Shoham et al. | |
| 2023/0157872 A1 | 5/2023 | Glozman et al. | |
| 2023/0165713 A1 | 6/2023 | Glozman et al. | |
| 2023/0240773 A1 | 8/2023 | Vaknin et al. | |
| 2024/0277425 A1 | 8/2024 | Beelen et al. | |
| 2025/0017676 A1 | 1/2025 | Korman et al. | |

FOREIGN PATENT DOCUMENTS

| | | |
|---|---|---|
| CA | 2860947 A1 | 2/2015 |
| CA | 2813403 C | 8/2017 |
| CA | 3026536 A1 | 2/2018 |
| CN | 107019559 A | 8/2017 |
| CN | 107693120 A | 2/2018 |
| CN | 105792783 B | 7/2019 |
| CN | 111281649 A | 6/2020 |
| CN | 111544198 B | 8/2020 |
| CN | 111839890 A | 10/2020 |
| CN | 109363832 B | 7/2021 |
| CN | 109549775 B | 9/2021 |
| CN | 113453642 A | 9/2021 |
| CN | 113490472 A | 10/2021 |
| EP | 3 410 995 A2 | 12/2018 |
| EP | 2 600 813 B1 | 1/2021 |
| EP | 3 328 334 B1 | 4/2021 |
| EP | 3 866 720 A1 | 8/2021 |
| EP | 3 471 675 B1 | 9/2021 |
| ES | 2704600 T3 | 3/2019 |
| JP | 5993376 B2 | 9/2016 |
| KR | 10-2010120183 A | 11/2010 |
| KR | 10-2021073542 A | 6/2021 |
| KR | 10-2021125985 A | 10/2021 |
| NL | 2004308 C2 | 8/2011 |
| RU | 2666116 C2 | 9/2018 |
| WO | WO-2010/064234 A2 | 6/2010 |
| WO | WO-2011/008922 A2 | 1/2011 |
| WO | WO-2011/060124 A2 | 5/2011 |
| WO | WO-2012/018796 A2 | 2/2012 |
| WO | WO-2012/037257 A2 | 3/2012 |
| WO | WO-2012/040442 A1 | 3/2012 |
| WO | WO-2014/197889 A1 | 12/2014 |
| WO | WO-2017/044965 A1 | 3/2017 |
| WO | WO-2018/219881 A1 | 12/2018 |
| WO | WO-2019/005921 A1 | 1/2019 |
| WO | WO-2019/049154 A1 | 3/2019 |
| WO | WO-2019/055701 A1 | 3/2019 |
| WO | WO-2019/108477 A1 | 6/2019 |
| WO | WO-2020/069080 A1 | 4/2020 |
| WO | WO-2022/023962 A2 | 2/2022 |
| WO | WO-2023/100125 A1 | 6/2023 |
| WO | WO-2024/201236 A1 | 10/2024 |
| WO | WO-2024/231879 A1 | 11/2024 |

OTHER PUBLICATIONS

International Search Report and Written Opinion issued in PCT Application No. PCT/US2019/032236 DTD Jul. 23, 2019, 9 pages.
Foreign Action other than Search Report on PCT PCT/US2019/032236 DTD Nov. 26, 2020.
Foreign Search Report on EP 19804319.2 DTD Nov. 23, 2021.
Attanasio et al.; Autonomy in surgical robotics; Annual Review of Control Robotics and Autonomous; 4; pp. 651-679; May 2021.
Chen et al.; Intraocular robotic interventional surgical system (IRISS): semi-autonated OCT-guided cataract removal; The international Journal of Medical Robotics and Computer Assisted Surgery; 14(6); e1949; DOI:10.1002/rcs. 1949; 14 pages; Dec. 2018.
Douglas; Robotic surgery in ophthalmology: reality or fantasy ?; British Journal of Ophthalmology; 91(1); p. 1; Jan. 2007.
Search Report on European Application No. 24196632.4 dated Feb. 14, 2025 (7 pages).
Verma; Can robotics be the future of ophthalmic surgery?; Journal of Robotic Surgery; 15(6); pp. 975-976; Dec. 2021.

(56) References Cited

OTHER PUBLICATIONS

Yu et al.; Robotic ocular ultramicrosurgery; Australian and New Zealand Journal of Ophthalmology; 26; pp. S6-S8; May 1998.

* cited by examiner

SYSTEM AND METHOD FOR AUTOMATED IMAGE-GUIDED ROBOTIC INTRAOCULAR SURGERY

CROSS-REFERENCE TO RELATED APPLICATIONS

This application is a national stage entry under 35 U.S.C. § 371 of International Application No. PCT/US2019/032236, filed May 14, 2019, which claims the benefit of U.S. Provisional Application No. 62/671,928, filed May 15, 2018, the contents of which are incorporated herein by reference in their entirety.

STATEMENT REGARDING FEDERALLY SPONSORED RESEARCH OR DEVELOPMENT

This invention was made with government support under Grant Number EY024065, awarded by the National Institutes of Health. The Government has certain rights in the invention.

TECHNICAL FIELD

This disclosure relates generally to automated image-guided robotic surgery.

BACKGROUND

With the development of femtosecond lasers and optical coherence tomography (OCT) imaging technologies, several surgical procedures involved in cataract surgery have been partially or fully automated. Certain laser-assisted platforms have the capability to perform accurate operations such as corneal incision, capsulotomy, and lens fragmentation. However, a critical operation—cataract lens extraction—still remains a manual operation. Indeed, the most common complications of cataract surgery—incomplete lens removal and posterior capsule rupture—occur during a stage when a fragmented cortical material is being removed by aspiration and phacoemulsification instruments. Automation of lens extraction by integration of visualization tools, assessing a complete removal of a cortical lens material, allowing real-time feedback to a surgeon, and allowing guided motion to prevent inadvertent collision can help decrease the incidence of surgical complications and improve surgical outcomes of cataract surgery.

It is against this background that a need arose to develop the embodiments described herein.

SUMMARY

In some embodiments, a surgical system includes: (1) an imaging device configured to acquire imaging data of a surgical site; (2) a surgical manipulator configured to hold a surgical tool; and (3) a controller connected to the imaging device and the surgical manipulator, wherein the controller is configured to receive the imaging data from the imaging device and derive, from the imaging data, an insertion trajectory for the surgical tool through an incision at the surgical site.

In additional embodiments, a controller to direct operation of a robotic surgical system includes a processor and a memory connected to the processor and storing instructions to: (1) direct acquisition of imaging data of a surgical site; and (2) derive, from the imaging data, an insertion trajectory for a surgical tool through an incision at the surgical site.

Other aspects and embodiments of this disclosure are also contemplated. The foregoing summary and the following detailed description are not meant to restrict this disclosure to any particular embodiment but are merely meant to describe some embodiments of this disclosure.

BRIEF DESCRIPTION OF THE DRAWINGS

For a better understanding of the nature and objects of some embodiments of this disclosure, reference should be made to the following detailed description taken in conjunction with the accompanying drawings.

DETAILED DESCRIPTION

System Integration

An image-guided intraocular surgical system of some embodiments is composed of an intraocular robotic surgical device, IRIS S, an OCT imaging device including an external, transpupillary OCT probe, and surgical instruments (see FIG. 1A), including an irrigation/aspiration tool controlled by an irrigation/aspiration device, Alcon ACCURUS. The IRISS device features mechanical fixed remote centers of motion (RCMs) (or pivot points), capability of fast tool change, and 4 degrees of freedom of surgical tool manipulation. The OCT imaging device provides three-dimensional (3D) volume scans of a tissue sample with a maximal scanning range of, for example, about 10 mm×about 10 mm×about 9.4 mm. A top view camera (e.g., a webcam) is embedded in the transpupillary OCT probe to observe a surgical field.

Figure 1A:
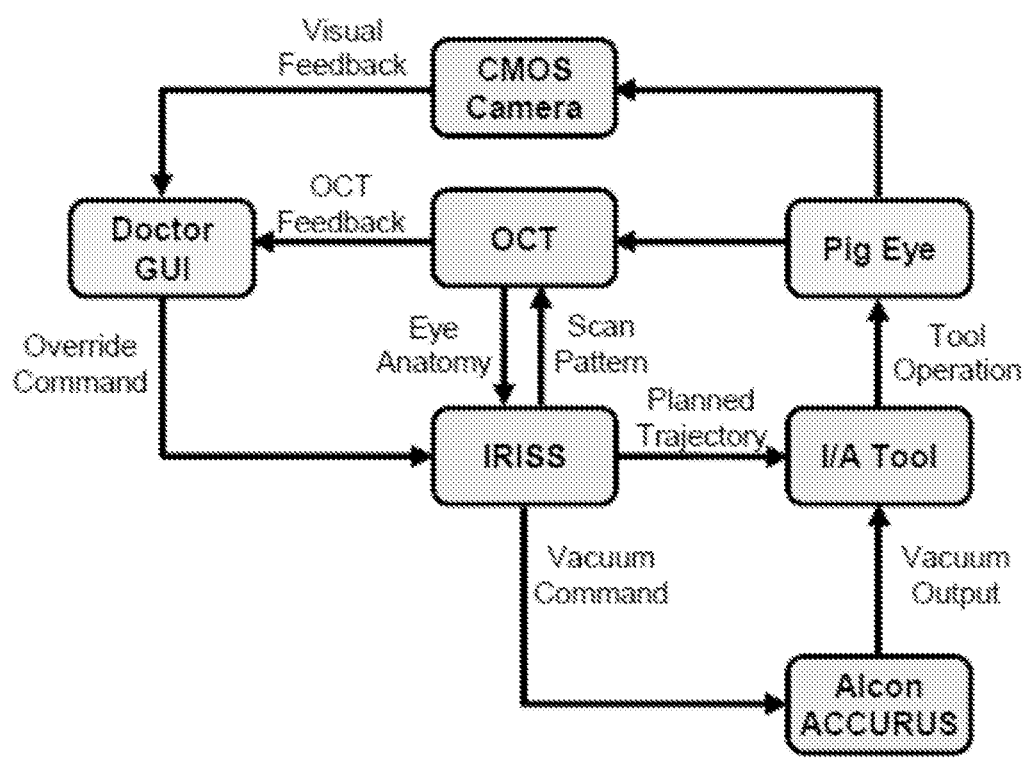
FIG. 1A. Schematic diagram of system integration.

As illustrated in FIG. 1A, the OCT device guides the IRISS device, along with a pre-surgical cataract-extraction tool trajectory, and allows for intraoperative surgical supervision and intervention by a surgeon. Both a tool motion and an aspiration force are autonomously controlled by the IRISS device. To prevent inadvertent contact or collision of a tool tip to tissues and posterior capsule, a no-fly zone is specified accordingly by an OCT-based anatomical model of an anterior segment of the eye.

Figure 1B:
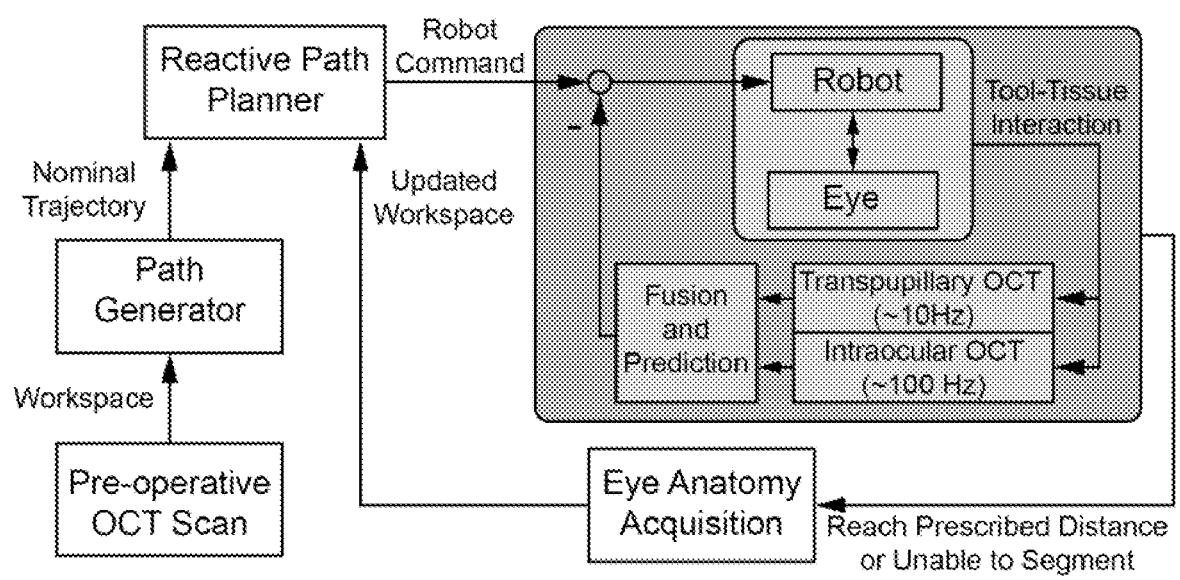
FIG. 1B. Schematic diagram of system integration for intraocular surgical procedures using feedback and sensory data from a transpupillary OCT probe together with an intraocular OCT probe.

In additional embodiments, as illustrated in FIG. 1B, an image-guided intraocular surgical system is configured to control and guide a surgical tool (e.g., position, orientation, and tool functionality) within an eye during intraocular surgical procedures using feedback and imaging data from a transpupillary OCT probe together with an intraocular OCT probe (e.g., an A-scan probe). The transpupillary probe can be located external to the eye and positioned above the eye during surgery, while the intraocular probe can be located inside the eye, alongside the tool or co-linear with the tool.

In such embodiments, the transpupillary OCT probe acquires high-resolution volume scans to acquire imaging data on an entire operating workspace (intraocular anatomy). From this data, an anatomical model of the workspace can be constructed and a nominal tool-tip trajectory can be derived. The processing of these volume scans can be relatively slow and imprecise (due to dynamic movement of the eye and tool), but provides a large-picture overview of the intraocular workspace from which the tool-tip trajectory can be derived.

In addition to the volume scans, the transpupillary OCT probe can perform a series of B-scans or A-scans around or intersecting the tool tip. For example, multiple (e.g., two) B-scans can be acquired: one along a tangential direction of a surgical path and the other in the normal direction. As another example, several A-scan lines can be acquired as a point cloud surrounding the tool tip or along a tool body. These scans can be used to extract anatomical features of interest. For example, from a B-scan, a two-dimensional curve can be extracted and used to infer relevant parameters of surgical interest, such as tool-to-tissue distance or anatomical feature shape and location. For single A-scan lines, depth information can be obtained alongside other metrics of interest.

In combination, the intraocular OCT probe, which can be mounted alongside the operating surgical instrument, co-linear with the operating surgical instrument, or separate from but adjacent to the surgical instrument, can monitor the tool tip position, orientation, and functionality together with the tool's vicinity. From imaging data acquired from the intraocular OCT probe, a type of imaged tissue can be identified and distinguished, and a distance (from the intraocular probe to the imaged tissue) can be derived. Further details on imaging data-based procedure to determine tissue type and distance between tissue and the intraocular OCT probe are provided below. The intraocular OCT probe can be an A-scan probe in some embodiments, although B-scan probes are also encompassed by this disclosure.

Processing of imaging data from the intraocular OCT probe can be fast (e.g., about 100 Hz) and accurate (e.g., to the level of OCT resolution) and image processing techniques can be used to improve identification accuracy. Imaging data acquired from the intraocular OCT probe can be used to update the anatomical model derived using the transpupillary OCT probe and improve the trajectory planning of the surgical tool. In addition, the tool functionality, such as vacuum force, irrigation force, micro-forceps pinching, and so forth, can be adjusted according to a tip-to-tissue distance as well as the identified tissue type.

An overall schematic of a control structure and procedure is depicted in FIG. 1B. At a top level, an objective can be to command a tool to perform a tool operation along a specified trajectory. A nominal tool path can be derived based on an anatomical model of the eye derived from transpupillary volume scans of a workspace. At an intermediate level, the objective can be to account for the dynamic nature of the workspace as well as tool-to-tissue interaction. This can be accomplished through a faster local update of the eye workspace in unvisited areas as well as a collision-avoidance and reactive path procedure. At a lowest level, an objective can be to move the tool along a prescribed path segment (a section of the trajectory) while controlling the tool functionality such that the tool-to-tissue distance or other parameter of interest that is regulated about a set point or tracked through a desired trajectory. By a separate feedback control loop, alternative tool functions can be controlled as well.

To account for processing delays, the procedure can include prediction functionality to allow the robotic surgical device to react in response to any detected or undetected changes in a surgical environment. To prevent or reduce the likelihood of aggressive tool motions or actions, a control objective and resultant actions can be properly formulated as well. To address communication and computation latency, if present, a Kalman predictor or other such prediction functionality can be used to account for topological variation in a spatial domain and tissue motion in a temporal domain. In the event a tool tip is occluded by an OCT-opaque anatomical feature or other surgical instrument, the intraocular OCT probe can be used to provide spatial cross-correlation for tissue identification along a tool axis direction.

Thus, embodiments provide for tool control during intraocular surgical procedures performed by a robotic-guided surgical system using OCT scans (e.g., transpupillary OCT scans, intraocular OCT scans, or both) to sense anatomical structures and provide a safe tool navigation scheme. Advantageously, embodiments can provide a surgeon with additional feedback and imaging information regarding anatomical structures in the vicinity of a tool during intraocular surgery. Furthermore, this information extends beyond pre-operative OCT scans (which provide an initial snapshot in time of an eye anatomy before surgery), and extends beyond intra-operative microscope images (which generally suffer from lack of visualization and insufficient depth perception). The information can be provided in visual overlays on a heads-up or heads-down display in an operating room.

Procedures for Automated Lens Extraction

Procedures for automated lens extraction include:
(A) OCT registration
(B) Automated alignment of the OCT device and the IRIS S device over the eye
(C) OCT scanning and modeling of an anatomical structure
(D) Automated lens extraction with real-time supervision and intervention The operations and details of these procedures are explained in the following.

Figure 1C:
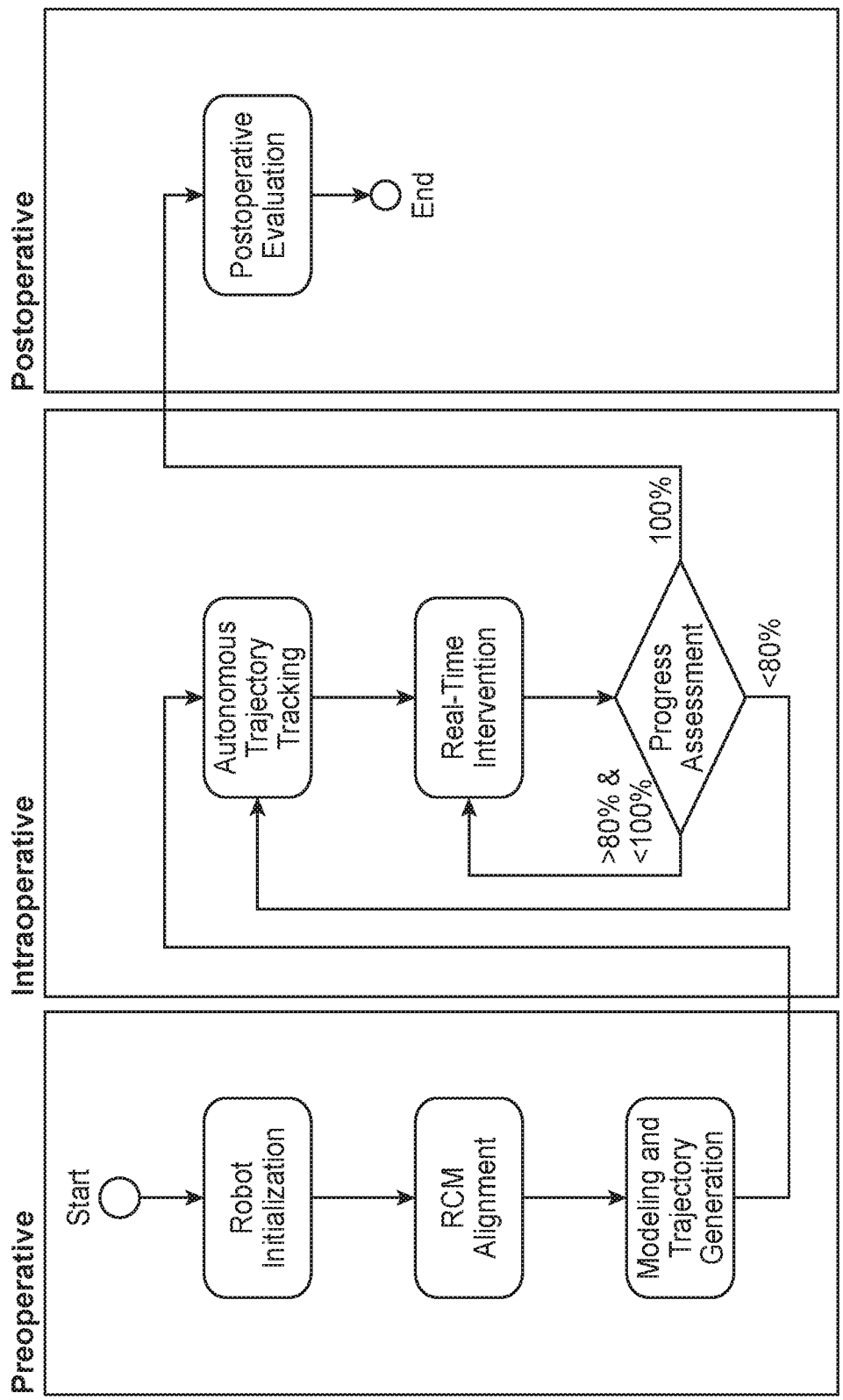
FIG. 1C. Flow chart of automated intraocular surgery.

In some embodiments, the procedures can be encompassed within an overall methodology including three stages: preoperative stage; intraoperative stage, and postoperative stage (FIG. 1C).

Procedure A: OCT Registration

Overview. For the purpose of controlling the IRISS device with OCT feedback, a relationship between an OCT reference frame and an IRISS reference frame is specified. To derive linear transformations (translation, rotation, and uniform scaling) from the OCT frame to the IRISS frame, Procrustes superimposition is performed. With the coordinate transformation specified, any point in the OCT reference frame can be converted to a point in the IRISS reference frame and vice versa.

Operation A1. Tool Tip Detection in the OCT Reference Frame

To derive the coordinate frame relationship, a procedure to localize a tool within OCT volume scans and determine a tool tip position is desired. A custom procedure is developed and is described here. With a cylindrical surgical tool (such as an irrigation-aspiration probe used throughout a surgery) within a scanning volume of the transpupillary OCT probe (e.g., about 10×about 10×about 9.4 mm), a medium-sensitivity (about 48 kHz) volume scan is performed. Each two-dimensional (2D) B-scan slice of the volume scan is converted from its raw intensity values to a grayscale image with a dynamically generated threshold level based on a predetermined reference intensity of the OCT volume scan. This conversion repeatedly results in a grayscale image that can be converted to binary with a constant threshold level such that—after reflection line removal and noise reduction—remaining white pixels can be assumed to be points on a surface of the tool. These points are converted to physical coordinates in the OCT frame based on a predetermined calibrated relationship. The points are then fitted with a cylinder and an axis of the fitted cylinder is considered to be a centerline of the tool.

To derive the tool tip position (a point on the determined centerline), the B-scan slices are evaluated from one side of the volume scan to its opposing side. In each B-scan, the largest binary blob size is used to determine which B-scans contain the tool and which do not. The B-scan that marks a transition from B-scans with the tool and those without is considered to be a plane that passes through the tip of the tool. The intersection of this tool tip plane and the determined tool centerline is the tool tip position. In some embodiments, the resolution of this procedure is between about 9.18-25 μm, depending on an orientation of the tool in the volume scan. A maximum resolution (e.g., about 9.18 μm) is determined from a resolution of A-scan lines; a minimum resolution (e.g., 25 μm) is determined from a distance between two B-scan slices in the volume scan.

Operation A2. Determination of the Coordinate Transformation Between the OCT Reference Frame and the IRISS Reference Frame To derive the desired coordinate frame relationship between the OCT device and the IRISS device, the IRISS device is directed to move through a series of, for example, n=13 poses. There are three criteria for selecting which points to use for this procedure: (1) They should form a unique, non-symmetric, 3D pattern, (2) They should be representational of a typical workspace of the robotic surgical device, and (3) They should be as few in number as practical without significantly compromising an accuracy of the coordinate transformation. From forward kinematics, the directed tool tip positions in the IRISS frame of each pose are derived or identified. At each pose, the tool tip position is also determined in the OCT frame from volume scans, as described in the previously described procedure. Thus, there are two representations of the same set of points: the tool tip positions in the IRIS S frame as derived from forward kinematics, and the tool tip positions in the OCT frame as derived from the OCT probe volume scans. To find the linear transformations (translation, rotation, and uniform scaling) from the OCT frame to the IRISS frame, Procrustes superimposition is performed. The resulting linear transformations are assembled into a 4×4 homogeneous transformation matrix (from the OCT frame to the IRISS frame) and inverted to find the inverse transformation (from the IRISS frame to the OCT frame). With the coordinate transformation derived, any point in the OCT reference frame can be converted to a point in the IRISS reference frame and vice versa.

To test the accuracy of this relationship, the IRIS S device is commanded to touch a series of n=30 randomly generated points within its typical workspace. At each point, a volume scan is taken, the tool tip position is derived from the volume scan of the OCT device, and an ideal tool tip position is derived from forward kinematics. The coordinate frame transformation is used to transform the tool tip positions derived in the OCT frame into the IRISS frame. Ideally, these points would perfectly overlap with zero error; in reality, some error can appear between each pair of points. This error is calculated as a 3D Euclidean distance between each pair of points. The statistical measures of the errors for a typical derivation of the coordinate transformation are shown in Table 1.

TABLE 1

Measures of Error in Typical Coordinate Transformation

| Min. [mm] | Mean [mm] | RMS [mm] | Max. [mm] | SD [mm] |
|---|---|---|---|---|
| 0.047 | 0.19 | 0.21 | 0.34 | 0.077 |

Procedure B: Automated Alignment of the OCT Device and the IRIS S Device Over the Eye Overview. Alignment procedure of the robotic surgical device over the eye is desired. A procedure is developed to automatically align the transpupillary OCT probe and the IRISS device relative to the eye such that (1) the OCT probe is well positioned for imaging a posterior capsule of a lens, (2) the tool tip will remain within a scanning volume throughout the entire lens removal, and (3) the mechanical RCM of the robotic surgical device is coincident with a Corneal Incision (CI).

Operation B1. The transpupillary OCT probe is aligned to the eye by an actuated XY stage using camera images as feedback. An optical center of the eye is detected from a high-sensitivity volume scan.

The goal of the alignment procedure is to optimally align the OCT volume scan to the eye such that (1) a center of the OCT volume scan is substantially coincident with the optical center (OC) of the eye, (2) a maximum volume of relevant anatomical features are captured in any arbitrary volume scan, and (3) the OCT probe is well positioned for imaging the posterior capsule and tool tip during automated lens removal.

Figure 2C:
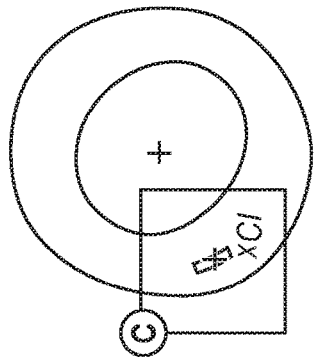
FIG. 2. Schematic of operations of alignment process. OCT probe position reference letters are shown as circled black letters.
Figure 2B:
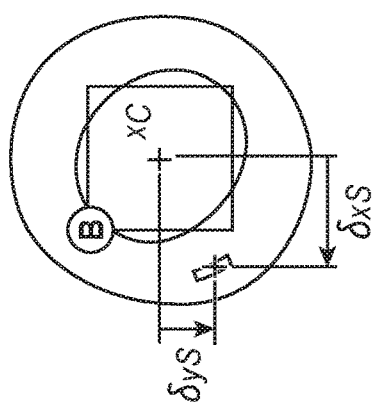
Figure 2A:
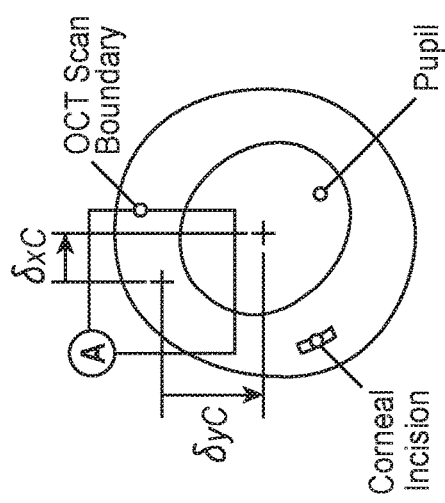

An approximate alignment is typically performed after the eye is prepared by a surgeon because environmental, surgical, and other actual conditions inhibit the realization of an ideal alignment. Therefore, a configuration (Position A) like that illustrated in FIG. 2(a) is more likely. With the eye and OCT probe in Position A (FIG. 2(a)), the integrated camera of the OCT probe is used to image the eye in real-time. Using visual guidance, the OCT stage is directed to move until the pupil is roughly (e.g., ≤about 0.2 mm) centered within the OCT scan boundaries. Upon completion, the configuration will be that of Position B; see FIG. 2(b). At this point, automated alignment is deemed complete and the position of the OCT stage is considered "centered." The eye center will then be detected from the high-sensitivity OCT volume scan at Position B.

Operation B2. The transpupillary OCT probe is translated over the CI and a high-sensitivity volume scan is obtained. From this volume scan, the CI is characterized and optimal insertion angles are derived. The location of the CI (invisible in the camera view) is derived from statistical surgical data.

To generate an optimal insertion trajectory, several important metrics regarding the CI are specified, involving a volume scan of the CI. However, for the majority of typically sized eyes, the CI is outside the OCT scan boundary in Position B and would not be imaged by the OCT probe; see FIG. 2(b). Therefore, statistical data are used to determine realistic translational displacements $\delta_{xS}$, $\delta_{yS}$, and $\delta_{zS}$ such that, after the OCT probe is moved by these displacements, the OCT scan volume is approximately positioned over the CI and to a scanning depth capable of imaging the CI. If no statistical data is available (for example, during the first few tests), "best guess" distances can be used instead. This position is called Position C and is shown in FIG. 2(c). If desired, online adjustment of the probe position can be granted to a surgeon during this motion; however, this may be unnecessary because a typical CI (approximate epithelium length of about 2-3 mm) readily fits within the OCT scan boundary (e.g., dimensions of about 10 mm×about 10 mm) and an approximate position suffices for a scan of acceptable quality.

With the OCT probe in Position C, a high-sensitivity volume scan is taken of the eye, hereafter referred to as the "CI volume scan." An automated procedure is performed on the CI volume scan to characterize the CI and derive metrics for planning an insertion trajectory. If the procedure fails to detect the CI in this operation, manual control can be granted to the surgeon to allow re-positioning of the probe as well as manual selection of the CI from the B-scans of the CI volume scan.

At this point, because the distances $\delta_{xS}$, $\delta_{yS}$, and $\delta_{zS}$ are identified (from OCT stage encoders), the OCT probe can be returned to Position B (the centered position). However, it is considered beneficial to keep it in Position C for the duration of the tool insertion to provide additional feedback on performance of the insertion. Note also that any displacement of the OCT stage can be automatically accounted by the coordinate transformations between the IRISS frame, the OCT frame, and an XYZ stage frame of the IRISS device.

In general, three sets of metrics and data are obtained in this operation:
 (1) Surgical performance characteristics
 (2) Optimal insertion angles, $\theta_1^*$ and $\theta_2^*$ (see FIG. 3), and location of CI, p*
 (3) Distances for optimal insertion trajectory, namely $w_I$ (see FIG. 4)

1. Surgical performance characteristics. From the CI volume scan, an incision epithelium length, an incision endothelium length, an incision depth, and a thickness of the cornea can be determined and recorded. Other metrics can be included if desired, and the volume scan is saved for future reference and analysis.

Figure 3B:
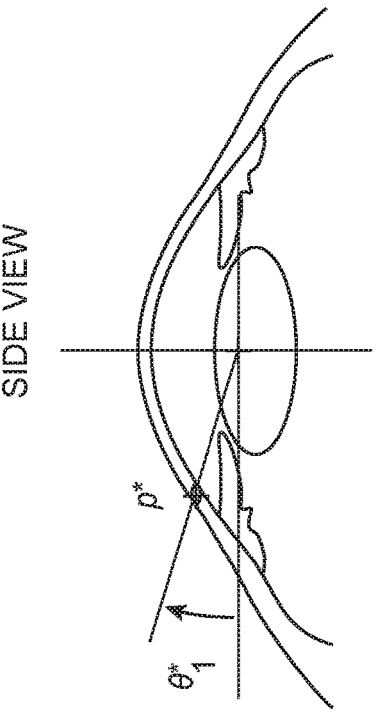
FIG. 3. Schematic of optimal insertion angles.
Figure 3A:
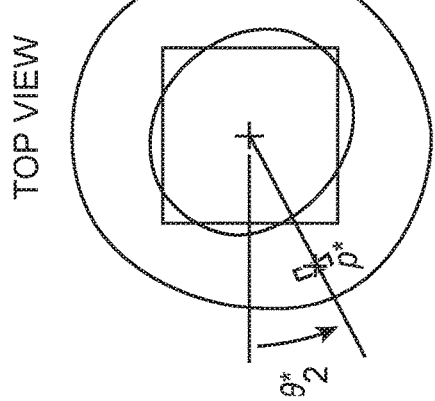

2. Optimal insertion angles and location of CI. The optimal insertion angles, $\theta_1^*$ and $\theta_2^*$, as well as the location in the IRISS frame of the CI, p*, can be derived, as shown in FIG. 3. $\theta_1^*$ is the optimal $\theta_1$ joint angle for insertion, $\theta_2^*$ is the optimal $\theta_2$ joint angle for insertion (ideally minimized), and p* is the optimal position for the mechanical RCM. Note that these values are determined in the OCT frame from the CI volume scan, but are converted to the IRISS frame for the use by the robotic surgical device.

3. Distances for optimal insertion trajectory. Several metrics are desired to determine an optimal insertion trajectory. To best understand these metrics, a schematic of a general insertion trajectory is shown in FIG. 4, with relevant variables indicated.

Figure 4:
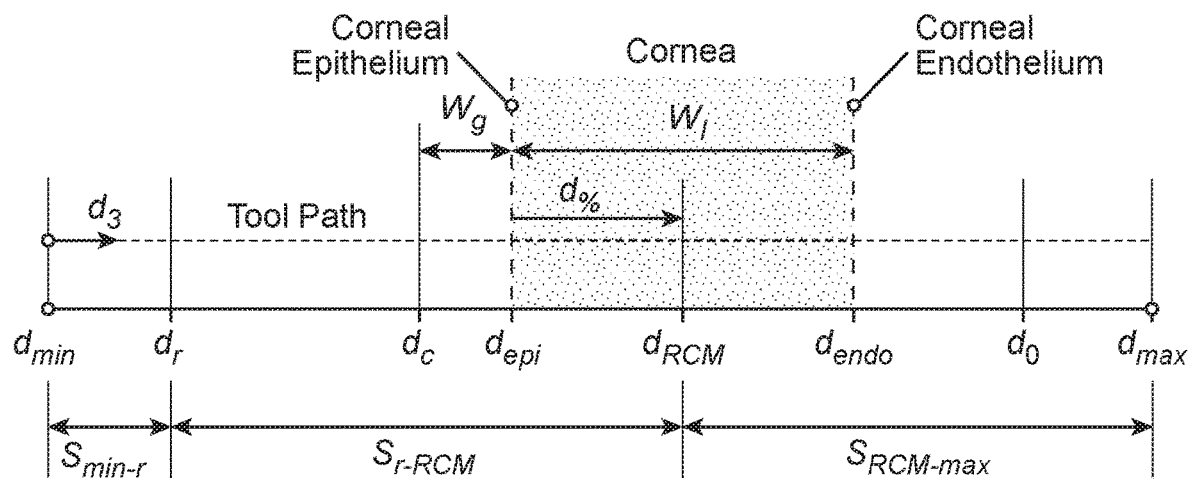
FIG. 4. Schematic of an optimal insertion trajectory. The dotted line represents the optimal insertion trajectory.

FIG. 4 shows the $d_3$ joint translation (tool tip displacement) over its entire range of motion.

$d_3=d_{min}=0$ is an extreme minimum joint distance and corresponds to a location of a homing sensor being triggered.

$d_3=d_r$ is a distance $s_{min-r}$ away from $d_{min}$ and is referred to as the "retracted position". This tool tip distance is used as a "safe" distance from the eye for the use in the OCT registration and a location to retract to during emergency extraction.

$d_3=d_c$ is the "clearance position" of the tool and is derived such that the tool tip is a distance $w_g$=about 1 mm away from the corneal epithelium (the anterior surface of the cornea). This position is used to provide visual confirmation that everything is "working correctly" before insertion is attempted.

$d_3=d_{epi}$ corresponds to the tool tip position just touching the corneal epithelium (the anterior surface of the cornea). Similarly, $d_3=d_{endo}$ is the tool tip distance along the insertion path such that the tool has passed through the cornea and the tip is at the corneal endothelium (the posterior surface of the cornea). The distance between $d_{epi}$ and $d_{endo}$ is $w_I$; note that this distance is not the thickness of the cornea, but rather a measure of the "depth" of the CI.

The tool tip displacement $d_3=d_0$ corresponds to the first point in the cataract-extraction trajectory.

Finally, the tool tip displacement $d_3=d_{max}$ corresponds to the maximum displacement of the tool (its joint limit) and is unlikely used in practice.

The three distances $s_{min-r}$, $s_{r-RCM}$, and $s_{RCM-max}$ are all identified beforehand from offline robot calibration; see bottom of FIG. 4. The correspondence between the theoretical trajectory shown in FIG. 4 and the anatomy from the CI volume scan is the overlap between $d_{RCM}$ and the mechanical RCM location within the IRISS frame. Therefore, for a complete registration, a designed RCM "depth" (d %) is specified. Physically, this is a measure of how "deep" the RCM is within the cornea. With a chosen d % value, the calibrated distances can be overlaid atop the measured anatomical distances from the CI volume scan.

The d % value is given as a percentage where $d_{epi} \leq d_{RCM} \leq d_{endo}$ and d %=0 means $d_{RCM}=d_{epi}$ and d %=100% means $d_{RCM}=d_{endo}$. In some embodiments, the optimal value of d % is derived from environmental and surgical conditions, and therefore the capability to adjust the value is desired.

With these metrics, tool insertion can be attempted.

Operation B3. The tool is inserted through the CI using the optimal insertion angles derived in Operation B2. If there is failure, the tool is retracted and Operation B2 is repeated or the tool is manually aligned by the surgeon.

The purpose of this procedure is to successfully insert the tool through the CI to point $p_a$ with minimal stress to the cornea and to do so in a single, fully automated operation. To realize this, the IRISS device is first directed to its retracted position ($\theta_1=\theta_2=\theta_4=0$ and $d_3=d_r$), if it is not already in this position. Next, the XYZ stage is directed such that the mechanical RCM is coincident with p*. This aligns the RCM to the CI. The IRISS device is then directed to $\theta_1=\theta_1^*$ and $\theta_2=\theta_2^*$ (optimal insertion angles), $d_3=d_c$ (clearance distance just outside the eye), and $\theta_4=0$.

Figure 5:
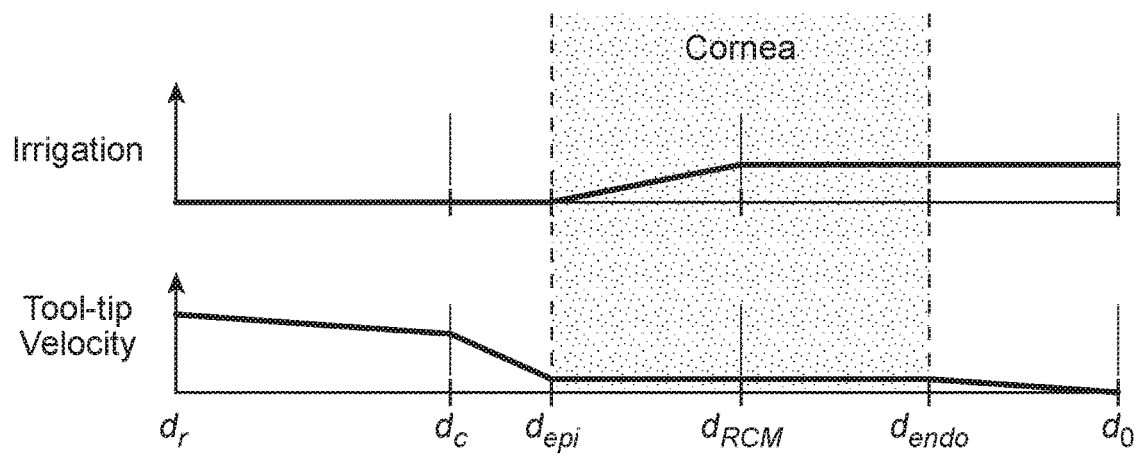
FIG. 5. Plot of aspiration force and tool tip velocity as a function of $d_3$ displacement. Note, $d_{min}$ and $d_{max}$ are not shown because the insertion trajectory uses $d_3=d_r$ as the initial displacement and $d_3=d_0$ as the final displacement.

At this operation, the IRISS motion is automatically paused and the tool tip position and IRISS pose are assessed by the surgeon. If acceptable, tool insertion is attempted. An emergency abort/override function is provided to the surgeon during the procedure to allow a safe retract from the eye if, for example, insertion is unsuccessful. During the automated insertion, an extent of applied irrigation and a tool tip velocity are a function of the $d_3$ displacement, as shown in FIG. 5.

If the insertion has failed (e.g., if the eye has collapsed, lost moisture, or so forth), then the tool is returned to the clearance position and manual control of the XYZ stage and joint angles are provided to the surgeon; namely the insertion procedure defaults to a surgeon-directed, manual process.

Once $d_3=d_0$, then insertion is considered complete and an automated cataract-extraction trajectory can be loaded and executed ($d_0$ is specified as the initial point of the cataract-extraction trajectory).

Note that there's a possibly faulty assumption here that the optimal insertion path obtained from the CI volume scan through the cornea is a line that passes through the RCM and point $d_3=d_0$. Most likely, this is not the case. This can be corrected by determining two line segments: one that represents the optimal trajectory through the cornea (the CI/RCM is on this line) and a second that connects the CI/RCM to the $d_0$ point. The tool can then be directed to pass along the first line segment until the tool tip has moved beyond the endothelium ($d_3>d_{endo}$), at which point $\theta_1$ and $\theta_2$ can be adjusted such that the tool now points directly at $d_0$. This adjustment is considered safe and sufficient because the tool extends through the RCM and the RCM is coincident with the CI (so stress is minimized).

Operation B4. The transpupillary OCT probe is translated back to its position at the end of Operation B1; namely, directly above the optical center of the eye. This operation is the reverse translation of Operation B2.

Procedure C: OCT Scanning and Modeling of the Anatomical Structure

Overview. To analyze the anatomy of the anterior segment of the eye, which is used to specify the tool tip trajectory and the no-fly zone, a modeling procedure applying OCT volume scans is developed. 3D image segmentation is performed on the OCT volume scans of the eye, and hyperbolic models are used to represent the cornea and posterior capsule. The pupil is also modeled as a 2D ellipse in 3D space.

Figure 6:
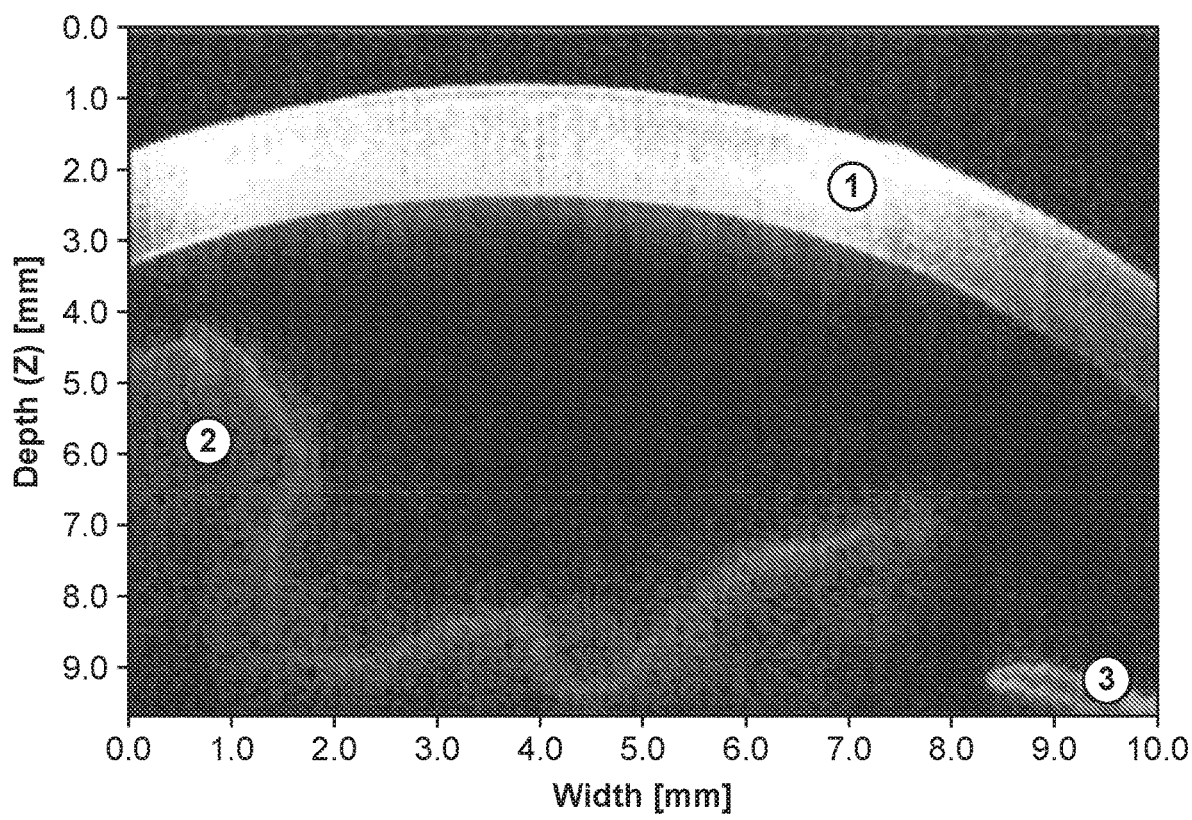
FIG. 6. OCT scan of upper anterior segment including (1) cornea, (2) lens material, and (3) iris.

To accommodate for a variation of different anatomical structure of eyes, a pre-operative OCT scan is introduced to parameterize an anatomical structure of the eye and then derive a constrained space where the tool tip can be safely navigated. High-sensitivity (e.g., about 5.5 kHz), 3D OCT volume scans (e.g., about 10×about 10×about 9.4 mm in air; the imaging depth in water will be decreased approximately by a factor of 1.35) are obtained of the anterior segment, including cornea, iris, and posterior capsule. Because the interested anatomical structure is greater (e.g., >about 9.4 mm along the z axis) than OCT's capable sensing range, the transpupillary OCT probe is moved up and down to cover the whole anterior segment of the eye. In Operation C1, the scan is first performed at a depth covering the cornea and the iris (FIG. 6). The posterior capsule is then imaged and modeled in Operation C2. The acquired data is then stitched together to formulate the entire anterior segment in Operation C3.

Operation C1. Translation of the transpupillary OCT probe along the z axis until the corneal epithelium is located in the range of 0 to about 3 mm of the OCT B-scan frame. Reconstruction of a cornea model from a high-sensitivity OCT volume scan.

After the OCT probe is moved such that the cornea epithelium is located in the range of 0 to about 3 mm of the OCT B-scan frame, a high-sensitivity volume scan is taken of the eye for modeling. With proper noise filtering, the intensity values of the 3D OCT volume data are converted to point cloud by automated binary thresholding. The remaining "true" voxels stand for part of the tissues which cause stronger reflection than water or vitreous liquid. OCT image segmentation is performed to extract the interested anatomical structure from the 3D point cloud data. To navigate the tool for automated lens removal, it is desired to determine the positions of the cornea and iris with respect to the CI that is already aligned with the RCM. Although other approaches for OCT image segmentation of anterior structures can be considered, a custom procedure is developed that considers a priori knowledge of the eye anatomy. For example, the cornea is generally located at the top of the eye, and the shape of the iris is similar to a ring in 3D space. Compared to other approaches that impose significant computational resource for accurate segmentation of tissues, the custom procedure is able to consume less time (e.g., about 1 minute) to derive a parameterized eye model for trajectory generation.

By least-square fitting on the segmented tissues, a second-order parabolic surface is used to represent the corneal epithelium along with the thickness of the cornea. Also, the range of the pupil encountered by the iris is modeled as a 2D ellipse in 3D space. These parameterized models define the space of the anterior chamber and will be used for surgical path planning in Procedure D. Note that due to an effective range of the aspiration force provided by the surgical tool (e.g., an irrigation/aspiration (I/A) hand-piece), a gap between tissues and the tool should be reserved when planning the surgical path. Therefore the effect of a stack error from segmentation and modeling can be alleviated as long as an error scale is relatively smaller than the gap.

Note that to enhance an image quality, viscoelastic material and/or water can be applied on the surface of the cornea to maintain good transparency before the OCT volume scan is taken.

Operation C2. Translation of the transpupillary OCT probe along z axis until the posterior capsule is located in the range of 0 to about 3 mm of the OCT B-scan frame. Reconstruction of a capsular and an iris model from a high-sensitivity OCT volume scan.

Figure 7:
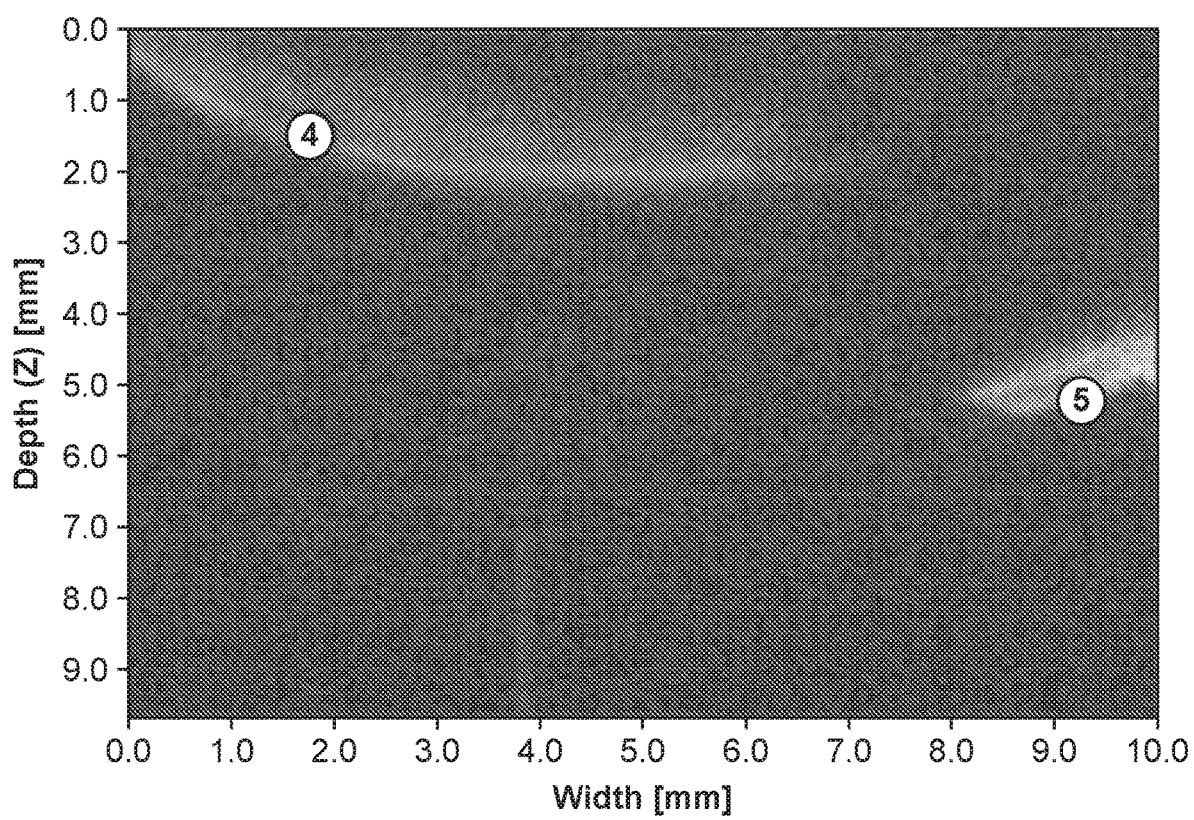
FIG. 7. OCT scan of lower anterior segment including (4) lens and posterior capsule and (5) inverted iris.

Similar to Operation C1, a second-order hyperbolic surface is used to represent the posterior capsule. Due to the finite imaging range of the OCT probe, an image of the iris appears inverted when moving down the OCT probe and searching for the posterior capsule. To avoid overlapping of the iris and the capsule, the OCT probe stops moving until the posterior capsule is located in the range of 0 to about 3 mm of the OCT B-scan frame, and the inverted iris is locating in the range of about 3 mm to about 9.4 mm (FIG. 7). Note that (1) a software program as used in Operation C1 can be applied here for deriving a parameterized model of the posterior capsule, because a second derivative of a polynomial surface model can distinguish the difference between cornea (concave down) and posterior capsule (concave up); and (2) the closer distance between the OCT probe and the iris allows for a clear image of the iris, and the iris model obtained in Operation C2 usually overrides the one obtained in Operation C1.

Operation C3. Merge the results obtained from Operations C1 and C2 based on the z displacement of the OCT probe.

When the OCT device performs either B-scans or volume scans, it assumes a medium that laser signals pass through is a constant. However, this is not necessarily true during cataract surgery. When a laser signal passes the corneal epithelium, the refractive index n would increase from 1 (in air) to approximately 1.35 (in water). This specifies the adjustment of a depth value (along z axis) detected from the OCT device:

$$z' = \begin{cases} z, & z < z_{epi} \\ z_{epi} + \dfrac{n_{air}}{n_{water}}(z - z_{epi}), & z \geq z_{epi} \end{cases} \quad (1)$$

where $z_{epi}$ is the depth of the corneal epithelium, and $n_{air}$ and $n_{water}$ are the refractive indices in air and water, respectively.

Figure 8:
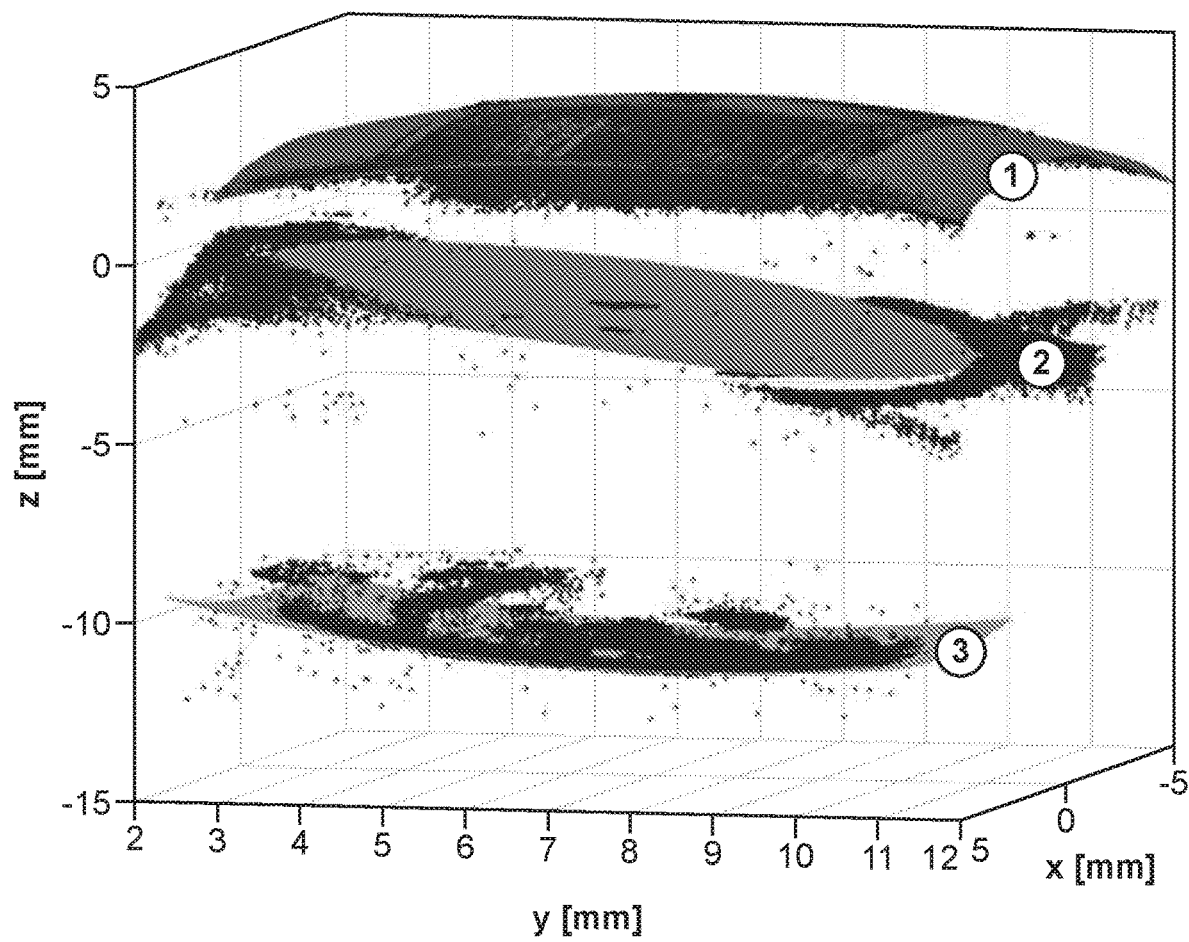
FIG. 8. Reconstructed eye model. (1) Reconstructed cornea, (2) reconstructed pupil, and (3) reconstructed posterior capsule. Points: raw OCT data.

A reconstructed anatomical model is thereby derived for planning a pre-surgical cataract-extraction trajectory (see FIG. 8).

Procedure D: Automated Lens Extraction with Real-Time Supervision and Intervention Overview. In this procedure, a tool tip trajectory is first derived from the eye model, and then is reviewed and adjusted (if appropriate) by the surgeon. Once approved, automated lens extraction is performed by tracking the pre-derived cataract-extraction trajectory and is evaluated periodically until lens material is substantially completely removed or the surgeon directs termination. Real-time monitoring and intervention is also available to the surgeon during the procedure. The surgeon is allowed to override command and control the surgical tool, adjust a speed of tool motion, and fine-tune an aspiration force during lens extraction.

Operation D1. Trajectory generation based on the reconstructed model of the anterior segment obtained in Procedure C. The surgeon reviews the trajectory and can fine-tune design parameters.

Figure 9A:
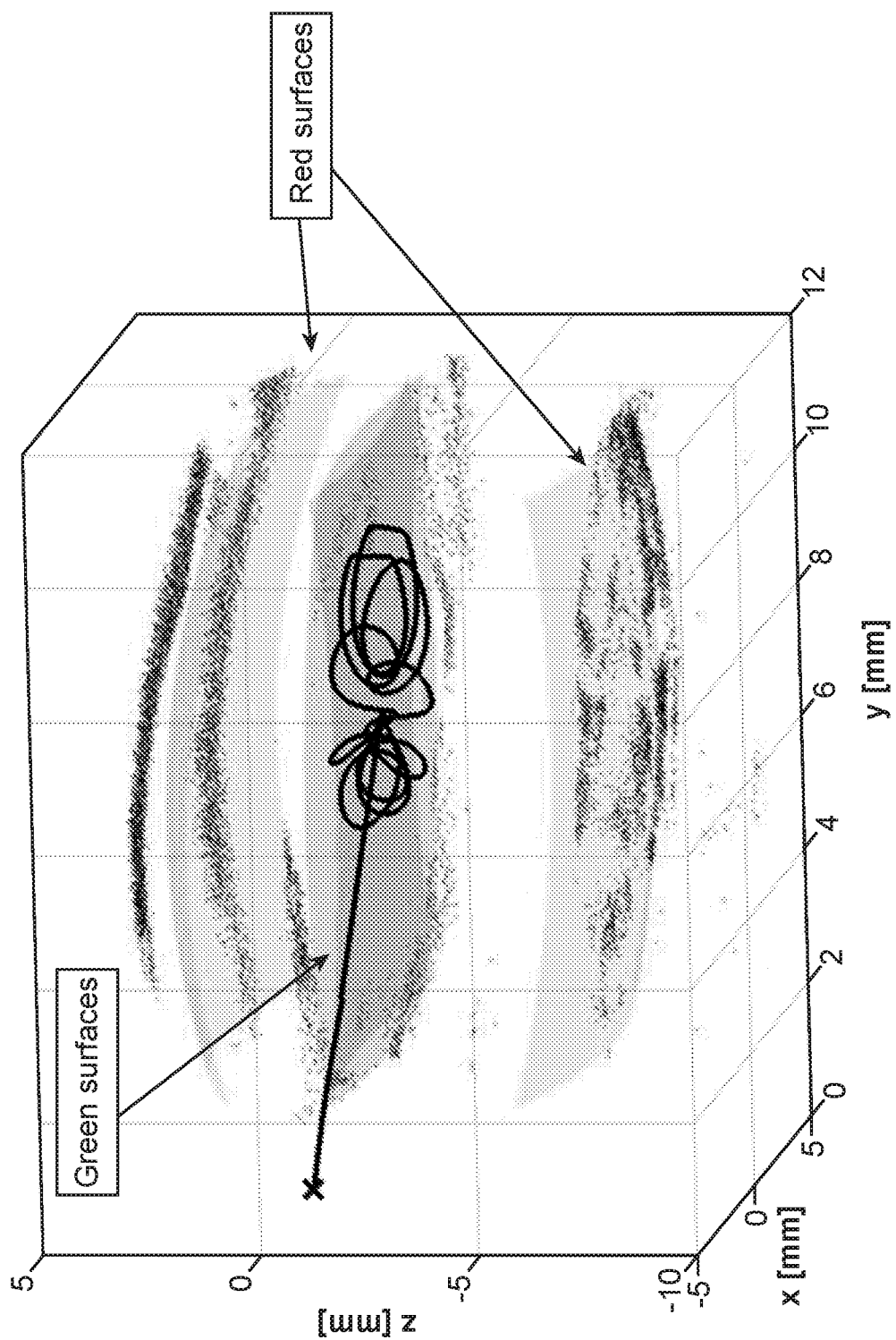
FIG. 9. Example Planned Trajectory in the IRISS frame. (a) Side view: Points: point cloud data from OCT volume scans; Red surfaces: no-fly zone; Green surfaces: a volume visited by a tool tip; Dark line: tool tip trajectory; X: the RCM. (b) Top view: Points: raw OCT data; Dark line: tool tip trajectory; X: the RCM; box: OCT scanning volume.
Figure 9B:
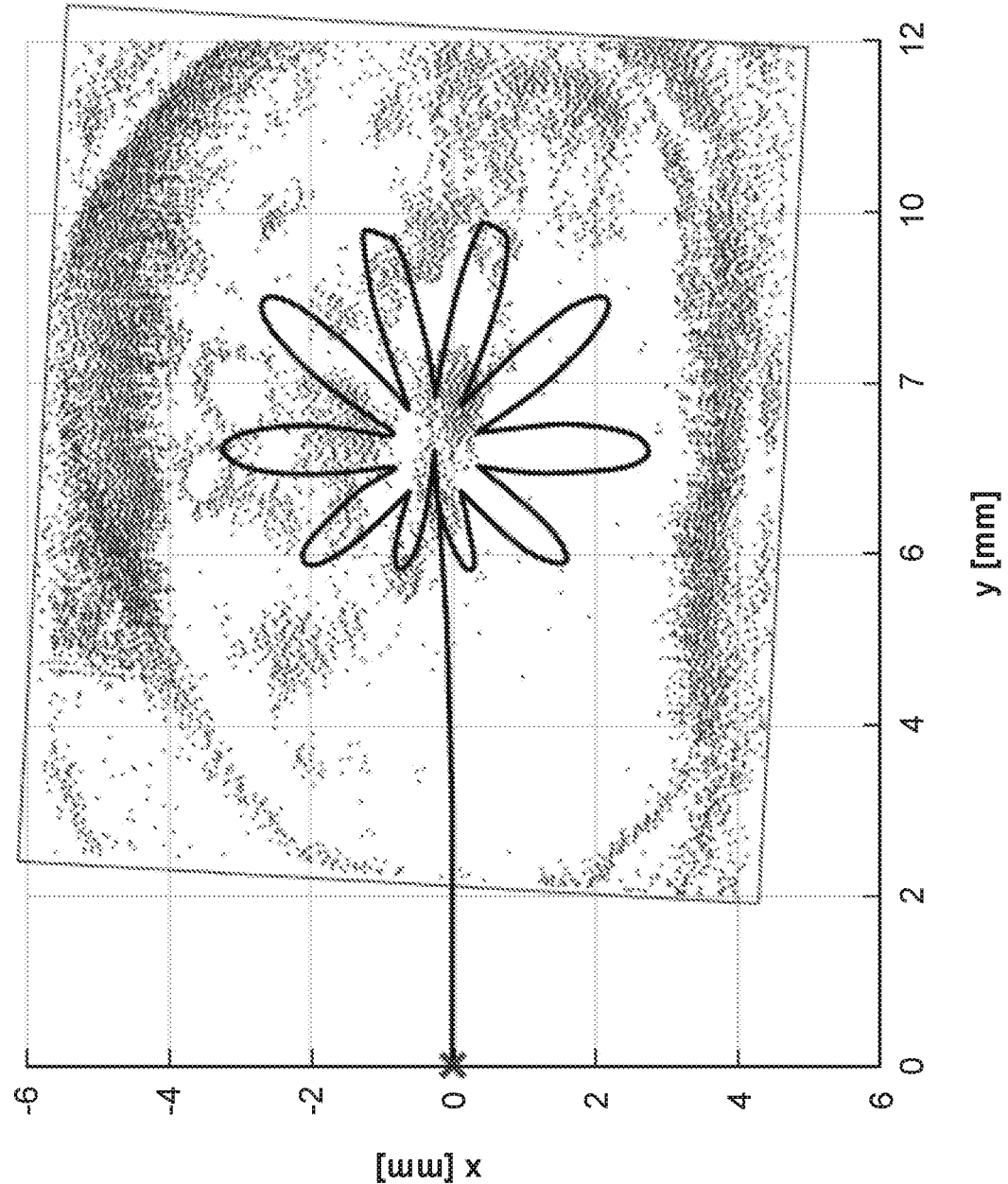

With the model of the anatomical structure of the eye, a pre-surgical tool tip trajectory is derived for automated lens removal (see FIG. 9). The tool tip trajectory design is associated with clinical criteria for cataract surgery, observations from manual lens removal, and also mechanical features of the IRIS S device. The most common complication, posterior capsule rupture, which occurs in about 1.8%-4.4% of cataract surgeries, may occur when there is either an inappropriate assignment of a tool tip position of an intraocular instrument relative to the posterior capsule or an inadequate control of an aspiration force when in close proximity to the capsule. Therefore, aside from tip position control, instrument rotation and aspiration force serve as two additional degrees of freedom for autonomous navigation.

A design pattern is proposed with the following characteristics: (1) Effective motion pattern designed for lens detachment and aspiration; (2) Prevention of posterior capsule rupture by progressively decreasing motion speed with distance from the tool tip to the posterior capsule; and (3) Dynamically programmed tool angle and aspiration force relative the tool tip position.

Figure 10:
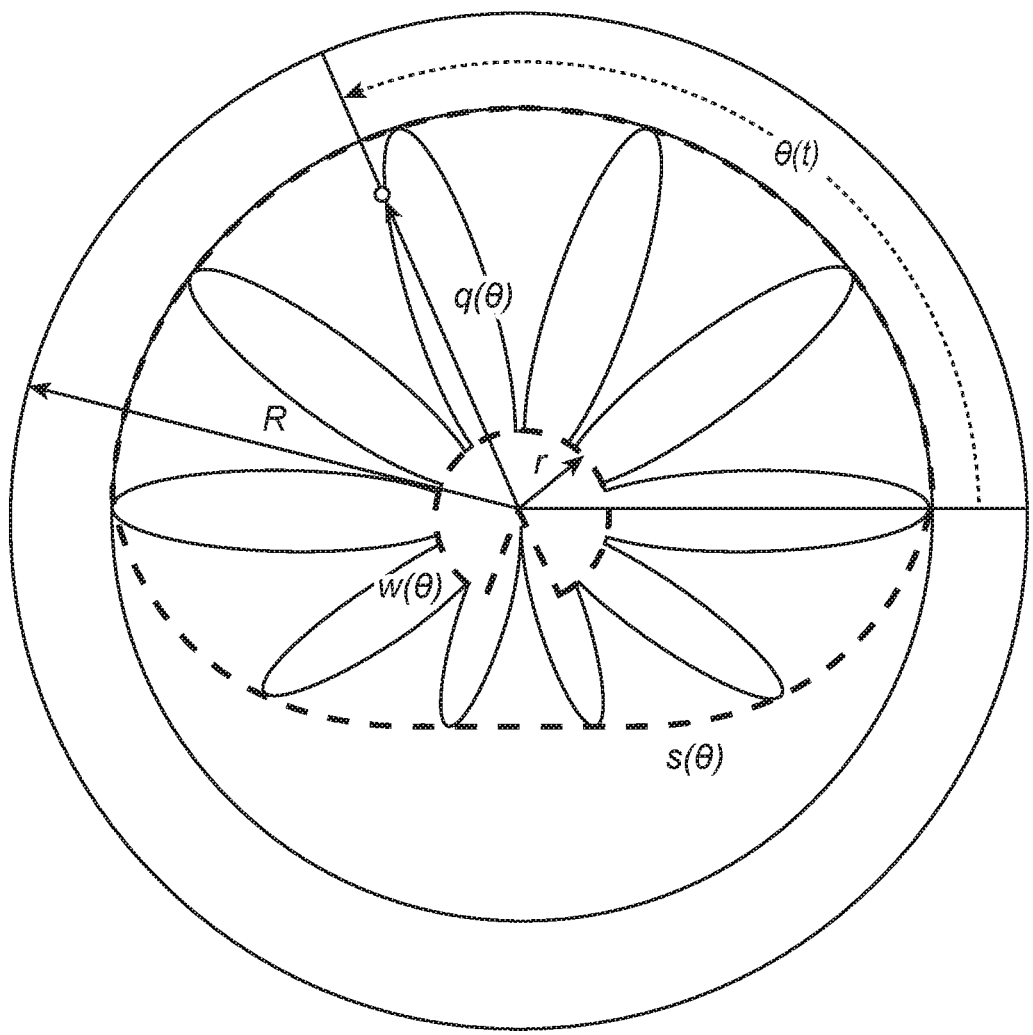
FIG. 10. Parameters for derivation of cataract-extraction trajectory.

Trajectory Pattern Design. A flower-shaped pattern with scooping motion is proposed, as in FIG. 10. The geometric shape in the plane of the pupil is designed to disaggregate conglomerated lens material, while the scooping motion is designed to detach lens material from the posterior capsule. Given a desired tool tip position, $$p(t) = [p_x(t)\, p_y(t)\, p_z(t)]^T, \text{ then} \quad (2A)$$

$$\begin{cases} p_x(t) = c_x + q\ \cos(\theta(t)) \\ p_y(t) = c_y + q\ \sin(\theta(t)) \\ p_z(t) = c_z - wa\ \sin(n\theta(t)) \end{cases}$$

where $c = [c_x\ c_y\ c_z]^T$ is the coordinate of the iris center, $w(\theta)$ is a window function between [0, 1] such that the trajectory will start and end at c, $a(\theta)$ is a position-dependent amplitude bounded by the distances to the anterior and posterior capsular surfaces, n is the number of lobes or "flower petals" in the geometric pattern, and $q(\theta)$ is the two-dimensional motion of the tool tip in polar coordinates specified as:

$$q(\theta) = (sR - wr)\sin^2\!\left(\dfrac{n\theta(t)}{2}\right) + wr \quad (2B)$$

where $s(\theta)$ is the radial scaling of the flower pattern which preserves the safety gap between the tool tip and iris, R is the pupil radius, r is the inner radius of the flower pattern, and $\theta(t)$ is the angle between the x-axis and a line from c to the tool tip in the range $[0, 2\pi]$. The value of $\theta(t)$ is chosen with equidistant sampling in polar coordinates with an approximately averaged tool tip velocity of 0.6 mm/s and cycle time of 90 s. From a top view, the pattern pivots near the incision point to disaggregate a conglomerated cortical material by increasing a longitudinal travel. The scooping motion is employed in a depth direction to ease the detachment of the lens from the posterior capsule.

A preponderance of motion in the y direction corresponds to an observed motion in $d_3$ from surgeon-operated master/slave experimental data. The relatively gradual change in the x direction, or correspondingly an incremental $\theta_2$ change, also serves to avoid a saturation in an actuator driving $\theta_2$ since position control for $\theta_2$ is more subjected to actuator saturation because of a relatively high overall gear ratio. Besides, a hard constraint is employed at each single joint to ensure a motion of the robotic surgical device does not exceed its constraints. For example, $\theta_1$ is constrained inside [about −8, about 35] degrees.

To detach the lens from the posterior capsule, the tool is moved slower and deeper after each cycle to detach and aspirate lens material. Therefore, the tool moves fastest for the first cycle (approximately averaged tool-tip velocity: 0.6 mm/s) and at a conservative, shallow depth (within about the top 30% of the capsular bag thickness). Each subsequent cycle progresses with the tool tip deeper (about +10% lens thickness per cycle) and slower (about −25% tool tip velocity).

Instrument Rotation. The I/A hand-piece (Millennium Surgical, 92-IA21 handle, 92-IA225 straight tip) has a side aspiration port at the tip. Posterior capsule rupture can occur when the cortical material is aspirated but the aspiration port still points at a capsular surface in close distance. For this reason, $\theta_4$ is scheduled such that the aspiration port is maintained facing away from the posterior capsule. Also, when the tool tip is near the equator of the capsular bag, the normal vector of the port is directed towards a virtual axis above the iris center c, $$\{(x,y,z) \in \mathbb{R}^3 : x = c_x \text{ and } z = c_z + \Delta z_a\} \quad (3A)$$

where $\Delta z_a > 0$ indicates the offset between the iris center and the virtual axis. The position-dependent instrument rotation can be described as:

$$\theta_4(t) = \text{atan } 2(p_x - c_x, p_z - c_z - \Delta z_a) \quad (3B)$$

where Atan 2( ) is the arctangent function with two arguments.

Figure 11:
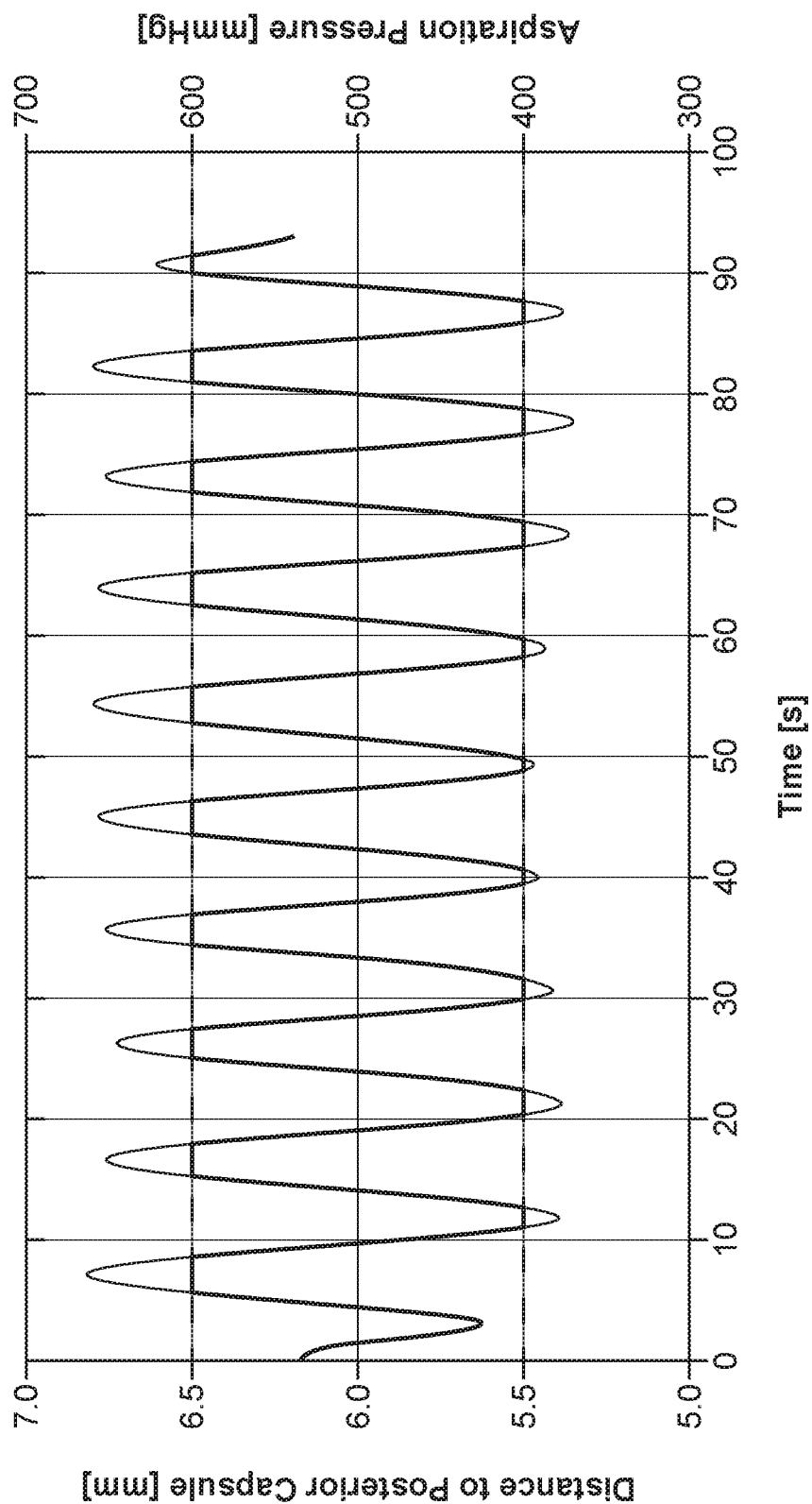
FIG. 11. An example of aspiration force profile scheduled along the tool tip trajectory with $z_{lb}=5.5$ mm, $z_{ub}=6.5$ mm, $f_{a,lb}=400$ mm Hg, and $f_{a,ub}=600$ mm Hg.

Aspiration Force Scheduling. The aspiration force is adjusted based on a distance to the posterior capsule to avoid posterior capsule rupture. When the tip is close to the posterior surface, the aspiration force is low; when it is away, the aspiration is increased accordingly. Thresholding is also desired for aspiration extremes so that it can stay effective without damaging tissues. Therefore, the aspiration is scheduled based on $\Delta z_p(t)$, the distance between the tool tip and the posterior capsule (FIG. 11). This is achieved by the following position-dependent aspiration scheduling:

$$f_a(t) = f_{a,lb} + (f_{a,ub} - f_{a,lb}) \text{ sat}\left[\frac{\Delta z_p(t) - z_{lb}}{z_{ub} - z_{lb}}\right] \quad (4)$$

where $f_a(t)$ is the aspiration force as a function of tool tip position; $(\ )_{lb}$ and $(\ )_{ub}$ are shorthand notations for the lower and upper bounds of a parameter; sat( ) is the saturation function with both domain and co-domain [0, 1]; and $z_{lb}$ and $z_{ub}$ are user-specified bounds on the magnitude of $\Delta z_p(t)$. This saturation is desired to prevent the aspiration force from becoming too aggressive or from deforming the intraocular tissue, while providing sufficient force to continue aspirating the lens material.

Once the pre-surgical trajectory has been derived and reviewed, a top view of the tool tip trajectory is projected on an anterior view of the eye in a graphical user interface (GUI). Likewise, a side view of the tool tip trajectory is projected on a superior view of the eye. If any adjustment is requested by a surgeon, offsets and range resizing can be manually performed.

Note that no aspiration is applied at this stage yet, but irrigation remains activated to maintain the pressure and thus the integrity of the eye anatomy as long as the tool tip remains inside of the anterior chamber.

Operation D2. Tracking of the pre-derived trajectory and activating the scheduled aspiration force. Real-time intra-operative monitoring and intervention is available to the surgeon.

Figure 12:
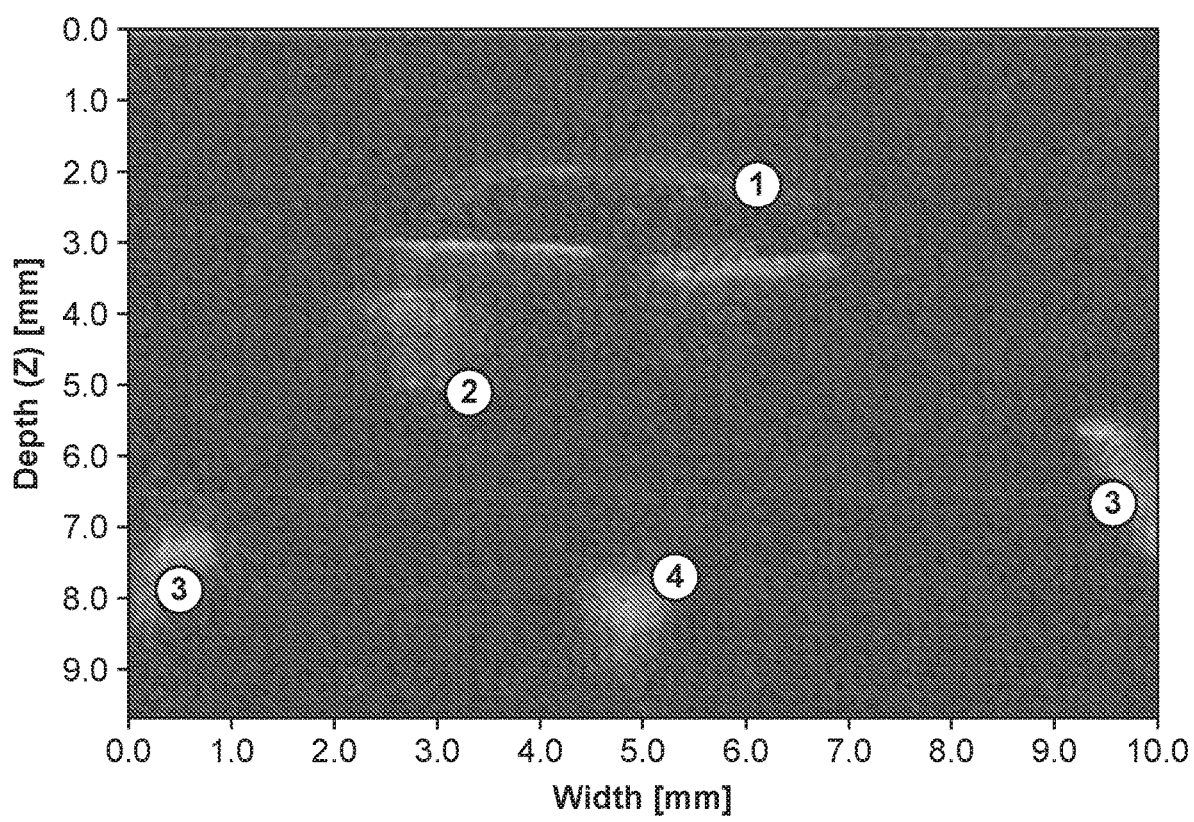
FIG. 12. An example of real-time OCT image feedback. Visible features are (1) the posterior capsule, (2) lens material, (3) the iris, and (4) the tool tip. Note: images are inverted.
Figure 13:
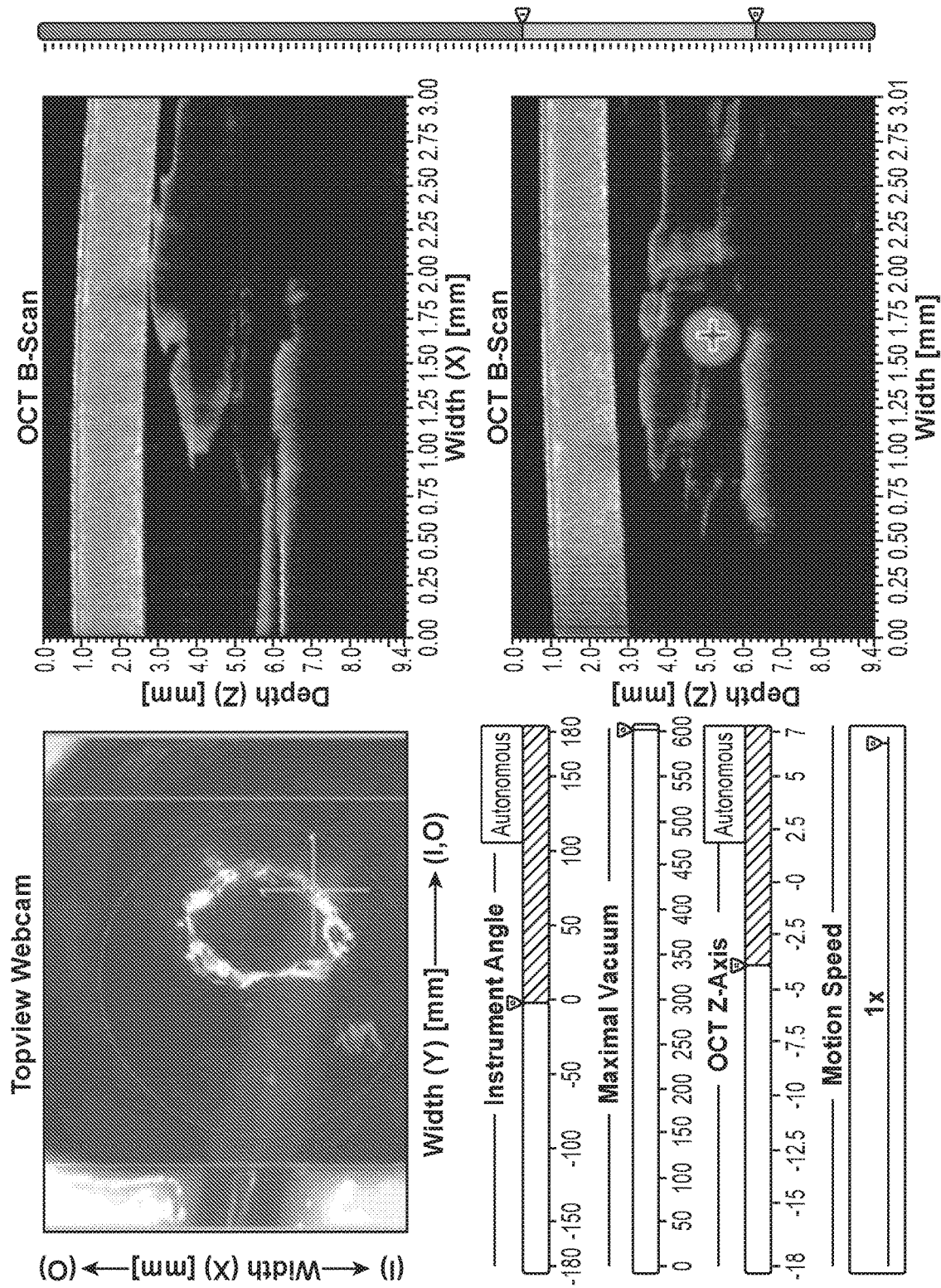
FIG. 13. User interface for intraoperative intervention.

During automated tracking of the cataract-extraction trajectory, real-time OCT B-scans or localized scans crossing the tool tip are obtained and displayed on the GUI for monitoring the surgical progress (see FIGS. 12 and 13). The OCT probe can also be translated to track the posterior capsule, lens material, or other features of interest. The frame rate of a B-scan (a time interval between each update without saving the data) is approximately 8 Hz and is set by a motion bandwidth of the mechanical galvo mirror. The frame rate of a localized scan volume is approximately 1.5 Hz.

Several options for surgical intervention are allowed:

(1) The surgeon can offset and resize the workspace of the trajectory. The trajectory p(t) is modified according to the adjusted workspace:

$$p'(t) = RS[p(t) - c] + T + c \quad (5)$$

where R and S are rotation and scaling matrices representing the workspace deformation, T is a translation vector representing the workspace translation, and the iris center c is the resizing center. This function is desired in the event of eye deformation or corneal collapse because, in such an event, the anatomical structure is different than that at the beginning of the surgery.

(2) The surgeon can modify the velocity at which the tool tip is navigated, or pause the motion while keeping the same aspiration force.

(3) The surgeon can override the scheduled rotation angle of the surgical instrument. This is sometimes desired to detach a lens piece from the posterior capsule and create disturbance which helps to aspirate larger lens materials.

(4) The surgeon can direct the robot to move the tool tip to any point inside the workspace by directly clicking on displayed images. The camera view determines the (x, y) coordinates of the target while the z coordinate is assigned from localized OCT B-scans. This function can be used to directly target and remove floating lens material and air bubbles. In the event a user requests a point outside the tool workspace or beyond the safety margins, a bisection procedure efficiently determines a boundary point closest to the desired target without formulating and solving a convex optimization problem. The tool tip will move towards the commanded point and then stop when its distance to the boundary is less than the threshold ε.

Inputs: Current position $p_0$, assigned position $p_{trg}$
Output: Feasible assigned point p*
Step 1: if $p_{trg}$ is inside workspace, return p*=$p_{trg}$
Step 2: $\Delta p = p_{trg} - p_0$
  $(\alpha_{lb}, \alpha_{ub}) = (0, 1)$ and p*=$p_0$
  do
    $p_{prev} = p^*$ $$\alpha = \frac{1}{2}(\alpha_{ub} - \alpha_{lb})$$

p*=$p_0 + \alpha \Delta p$
    if p* is out of bounds. $\alpha_{ub} = \alpha$
    else $\alpha_{lb} = \alpha$
    end if
  while ($\|p^* - p_{prev}\|_2 > \epsilon$) or (p* is out of bounds)
  return p*

(5) The surgeon can request emergency termination of the surgery. The instrument will retract from the eye within, for example, about 200 ms.

Operation D3. Evaluation of OCT scans at the anterior segment every about two minutes to determine whether and how to continue the lens extraction.

Figures 14A, 14B, 14C:
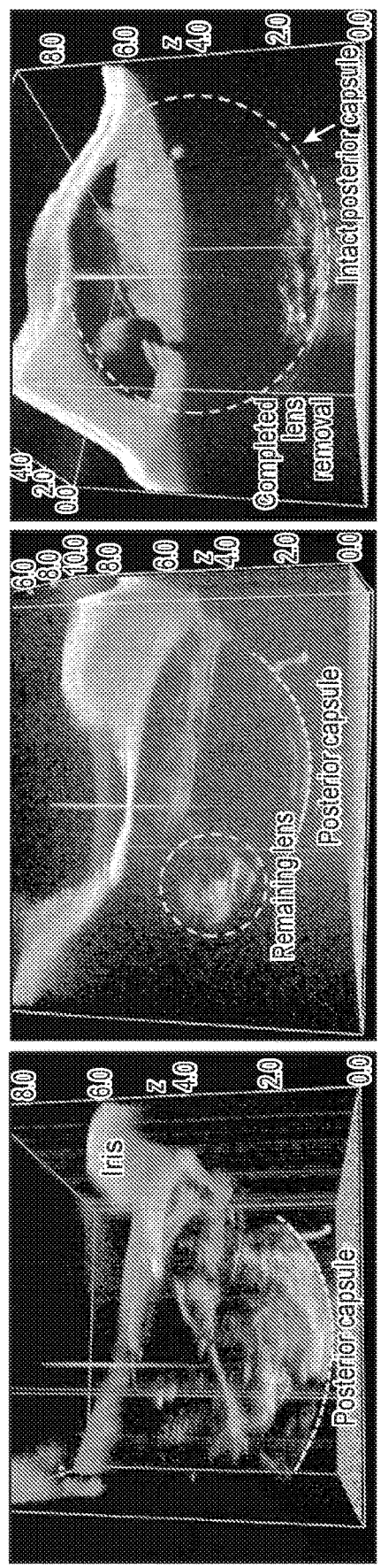
FIG. 14. Intraoperative evaluation every about two minutes. (a) After about 2 minutes. (b) After about 4 minutes. (c) After completion.

Evaluation of progress (e.g., performed by human surgeon or by computer vision procedure) every about two minutes by pausing the tool motion at a standby position and obtaining an OCT volume scan (FIG. 14). Naked eye inspection can be performed if desired. Multiple motion options are provided to allow user selection of a following autonomous mode based on the evaluation result: (1) continuing the pre-derived trajectory if most of the lens still remains in the anterior segment (FIG. 14(a)) (2) moving to the locations of remaining lens if there are just a few floating minute particles (FIG. 14(b)). Lens extraction is completed when substantially no cortical materials are left in the anterior segment (FIG. 14(c)) or no progress can be made (judged by the surgeon, usually because of the malfunction of the I/A tool or attachment of the lens onto the posterior capsule).

The automation procedures extend beyond master-slave operation to achieve high precision instrument manipulation. Also, the robust dynamic coordinate transformation is computationally more tractable compared to a stereo-assisted OCT approach for tool tip tracking. Regarding the use of OCT imaging, intermittent 3D volume scans, assisted with real-time B-scans and top camera views, also afford improved evaluation/guidance of automated lens removal.

Use of Intraocular OCT Probe to Guide Tool. In combination with the transpupillary OCT probe, intraoperative imaging data acquired from an intraocular OCT probe can be used to update the anatomical model derived using the transpupillary OCT probe and adjust the trajectory of tool motion. In addition, tool functionality can be adjusted according to a tip-to-tissue distance as well as an identified tissue type.

Figure 15:
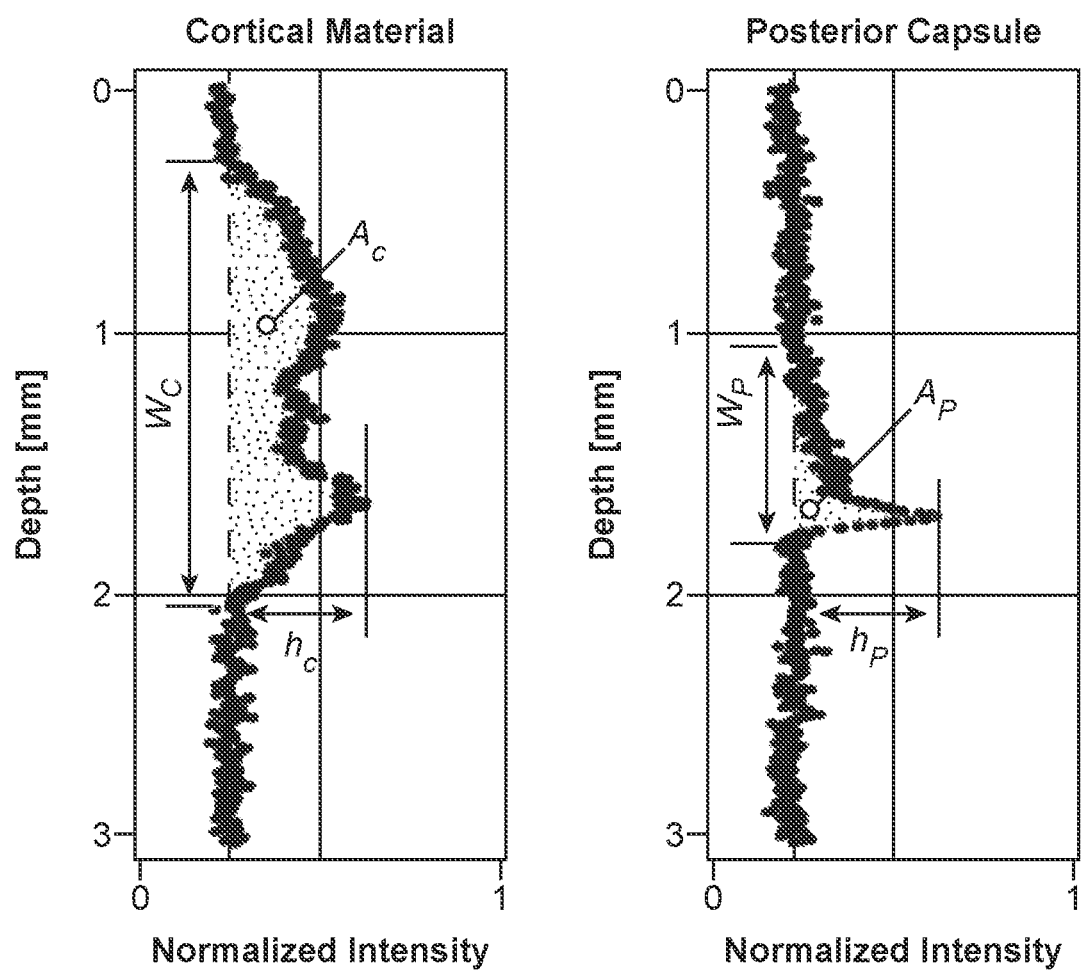
FIG. 15. Imaging data-based procedure to determine tissue type and distance between tissue and an intraocular OCT probe. A dashed line represents a baseline (background noise); $w_c$ is a width of an intensity above the baseline; $A_c$ is an area of the intensity above the baseline; and $h_c$ is a maximum height/peak of the intensity above the baseline. These measurable parameters are characteristic of an imaged anatomical tissue and can be used to identify and distinguish the tissue.

An imaging data-based procedure to determine tissue type and distance between tissue and the intraocular OCT probe is explained in connection with FIG. 15. Tissue identification can be performed on an anatomical feature of interest using the intraocular OCT probe. In the case of an A-scan probe, identification can be performed from temporal A-scan lines based on a differentiation of return signal strength between a tissue of interest and a surrounding tissue or a surrounding liquid medium (e.g., balanced salt solution, deionized water, viscoelastic fluid, or another surgical or biological fluid). Different tissues exhibit distinct A-scan characteristics, which facilitates the segmentation and identification process. As an example, FIG. 15 illustrates a difference in signal strength between a cortical material and a posterior capsule during a surgical procedure. The cortical material exhibits a wide (irregular) spatial coverage, a lower reflection, and a higher diffusion while the posterior capsule exhibits a narrow (unimodal) distribution, a higher reflection, and a lower diffusion.

Robotic Surgical Device

Figure 16:
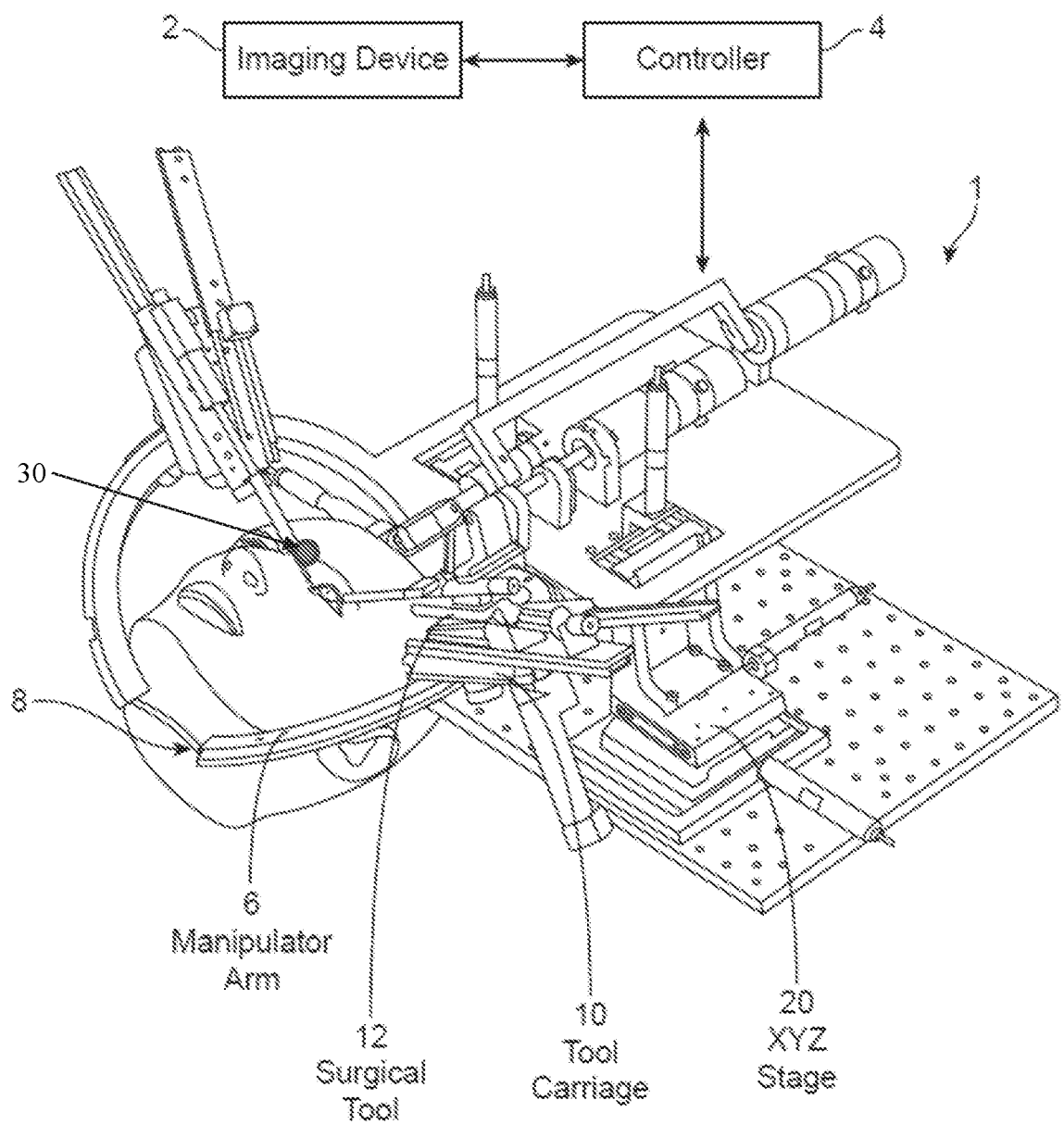
FIG. 16. A robotic surgical device according to some embodiments.

FIG. 16 shows a robotic surgical device according to some embodiments. The device includes a surgical manipulator 1 and a controller 4. The controller 4 is connected to the surgical manipulator 1 and an imaging device 2, and directs operation of the surgical manipulator 1 and the imaging device 2. The controller 4 can be implemented as a processor and an associated memory storing instructions executable by the processor. The imaging device 2 includes an OCT imaging device, which includes a transpupillary OCT probe.

As shown in FIG. 16, the surgical manipulator 1 includes a pair of independently controllable manipulator arms 6, each including a semi-circular track 8 to which the tool carriage 10 is moveably mounted, and where the tool carriage 10 holds one or more surgical instruments or tools 12 that are moveably mounted to the tool carriage 10. Each surgical tool 12 is mechanically constrained about a RCM of the manipulator arm 6 to which the surgical tool 12 is mounted, such that that an axis or centerline of the surgical tool 12 extends through the RCM while remaining in a planar region specified based on a rotational orientation of the manipulator arm 6. As shown in FIG. 16, the imaging device 2 also includes an intraocular imaging probe 30, such as an intraocular OCT probe, which is mounted alongside a surgical tool 12 to acquire intraoperative imaging data. Robotic motion of various components of the manipulator arms 6 is driven by actuators, such as motors and associated drive electronics, as directed by the controller 4. Although the two manipulator arms 6 are shown in the FIG. 16, more than two or a single one of such manipulator arms 6 can be included in other embodiments.

Figure 17:
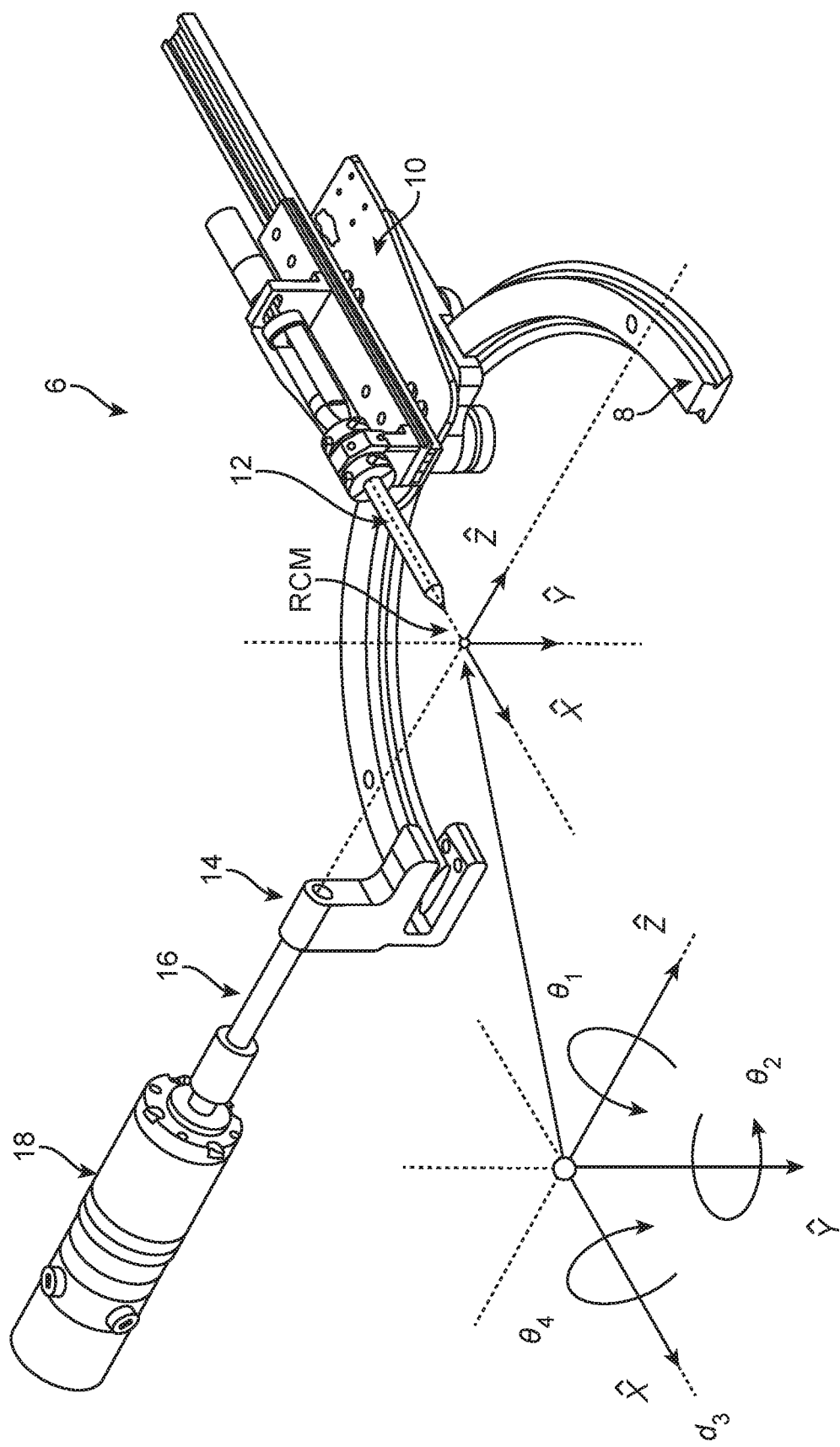
FIG. 17. A manipulator arm included in a robotic surgical device according to some embodiments.

A single one of the manipulator arms 6 is shown in FIG. 17, according to some embodiments. Additional manipulator arms 6 can be similarly configured as explained below. The RCM of the manipulator arm 6 is mechanically enforced by mounting the surgical tool 12 to the tool carriage 10 that is slidable along the semi-circular track 8, allowing rotation about $Y^\wedge$ by $\theta_2$. The semi-circular track 8 is mounted to a rotational joint 14, which allows rotation about $Z^\wedge$ by $\theta_1$. The semi-circular track 8 and the rotational joint 14 are aligned such that their rotational axes are substantially orthogonal and intersect at the RCM. The surgical tool 12 is mounted such that its axis or centerline intersects the axis of rotation of the semi-circular track 8 and passes through the RCM. In this way, in-and-out translational motion of the tool 12 is denoted as $d_3$, and rotation of the tool 12 about its centerline is denoted as $\theta_4$. The semi-circular track 8 is mounted, via the rotational joint 14, to a rotational shaft 16 that is driven to rotate by an actuator 18, such as a motor and associated drive electronics. An axis of rotation of the shaft 16 is substantially coincident with the axis of rotation of the rotational joint 14.

Referring back to FIG. 16, to allow three-dimensional translation of the mechanically constrained RCMs, the manipulator arms 6 are mounted to a multi-axis positioning stage 20 capable of three-dimensional XYZ translation. Translational motion of the stage 20 is driven by a set of actuators, such as motors and associated drive electronics.

EXAMPLE EMBODIMENTS

The following are example embodiments of this disclosure.

First Aspect

In some embodiments, a surgical system includes: (1) an imaging device configured to acquire imaging data of a surgical site; (2) a surgical manipulator configured to hold a surgical tool; and (3) a controller connected to the imaging device and the surgical manipulator, wherein the controller is configured to receive the imaging data from the imaging device and derive, from the imaging data, an insertion trajectory for the surgical tool through an incision at the surgical site.

In some embodiments, the controller is configured to derive the insertion trajectory by performing a coordinate transformation between a reference frame of the imaging device and a reference frame of the surgical manipulator.

In some embodiments, the controller is configured to derive the insertion trajectory by deriving, from the imaging data, a set of insertion angles for the surgical tool through the incision.

In some embodiments, the controller is configured to derive the insertion trajectory such that a remote center of motion of the surgical tool is coincident with the incision.

In some embodiments, the controller is configured to derive the insertion trajectory by directing translation of the imaging device relative to the incision.

In some embodiments, the controller is configured to derive the insertion trajectory by deriving a set of distances indicative of an extent of displacement of a tip of the surgical tool along the insertion trajectory.

In some embodiments, the controller is configured to direct translation of the surgical manipulator to translate the surgical tool along the insertion trajectory.

In some embodiments, the controller is configured to direct a variation of a speed of translation of the surgical tool as a function of the extent of displacement of the tip of the surgical tool along the insertion trajectory.

In some embodiments, the controller is configured to direct movement of the surgical manipulator to move the tip of the surgical tool along a tissue extraction trajectory.

In some embodiments, the controller is configured to derive the tissue extraction trajectory according to a parameterized model of the surgical site.

In some embodiments, the controller is configured to derive the parameterized model of the surgical site from the imaging data of the surgical site.

In some embodiments, the parameterized model of the surgical site specifies a volume within which the tissue extraction trajectory is confined.

In some embodiments, the parameterized model of the surgical site specifies a set of surfaces between which the tissue extraction trajectory is confined.

In some embodiments, the imaging device includes a transpupillary imaging probe, and the controller is configured to derive the parameterized model of the surgical site from imaging data acquired by the transpupillary imaging probe.

In some embodiments, the imaging device further includes an intraocular imaging probe, and the controller is configured to update the parameterized model of the surgical site from imaging data acquired by the intraocular imaging probe.

In some embodiments, the controller is configured to identify a tissue adjacent to the tip of the surgical tool from the imaging data acquired by the intraocular imaging probe.

In some embodiments, the controller is configured to derive a distance between the tip of the surgical tool and a tissue adjacent to the tip of the surgical tool from the imaging data acquired by the intraocular imaging probe.

In some embodiments, the surgical tool is an aspiration tool, and the controller is configured to direct a variation of an aspiration force of the surgical tool as a function of a position of the tip of the surgical tool along the tissue extraction trajectory.

In some embodiments, the controller is configured to direct a variation of a rotation angle about a centerline of the surgical tool as a function of a position of the tip of the surgical tool along the tissue extraction trajectory.

In some embodiments, the imaging device includes an intraocular imaging probe, and the controller is configured to adjust functionality of the surgical tool according to imaging data acquired by the intraocular imaging probe.

In some embodiments, the controller is configured to provide a user interface to visualize the surgical site for intraoperative monitoring and to provide an override function to adjust or terminate movement of the surgical tool along the tissue extraction trajectory.

In some embodiments, the controller is configured to provide a user interface to visualize the surgical site for evaluation of surgical progress.

In some embodiments, the user interface provides a function to select a following autonomous mode according to surgical progress.

Second Aspect

In additional embodiments, a controller to direct operation of a robotic surgical system includes a processor and a memory connected to the processor and storing instructions to: (1) direct acquisition of imaging data of a surgical site; and (2) derive, from the imaging data, an insertion trajectory for a surgical tool through an incision at the surgical site.

In some embodiments, the memory further stores instructions to direct translation of the surgical tool along the insertion trajectory.

In some embodiments, the memory further stores instructions to direct movement of a tip of the surgical tool along a tissue extraction trajectory.

As used herein, the singular terms "a," "an," and "the" may include plural referents unless the context clearly dictates otherwise. Thus, for example, reference to an object may include multiple objects unless the context clearly dictates otherwise.

As used herein, the term "set" refers to a collection of one or more objects. Thus, for example, a set of objects can include a single object or multiple objects. Objects of a set also can be referred to as members of the set. Objects of a set can be the same or different. In some instances, objects of a set can share one or more common characteristics.

As used herein, the terms "connect," "connected," and "connection" refer to an operational coupling or linking. Connected objects can be directly coupled to one another or can be indirectly coupled to one another, such as via one or more other objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, a first numerical value can be "substantially" or "about" the same as a second numerical value if the first numerical value is within a range of variation of less than or equal to ±10% of the second numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, concentrations, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a range of about 1 to about 200 should be understood to include the explicitly recited limits of about 1 and about 200, but also to include individual values such as about 2, about 3, and about 4, and sub-ranges such as about 10 to about 50, about 20 to about 100, and so forth.

While the disclosure has been described with reference to the specific embodiments thereof, it should be understood by those skilled in the art that various changes may be made and equivalents may be substituted without departing from the true spirit and scope of the disclosure as defined by the appended claims. In addition, many modifications may be made to adapt a particular situation, material, composition of matter, method, operation or operations, to the objective, spirit and scope of the disclosure. All such modifications are intended to be within the scope of the claims appended hereto. In particular, while certain methods may have been described with reference to particular operations performed in a particular order, it will be understood that these operations may be combined, sub-divided, or re-ordered to form an equivalent method without departing from the teachings of the disclosure. Accordingly, unless specifically indicated herein, the order and grouping of the operations are not a limitation of the disclosure.

What is claimed is:

1. A surgical system comprising:
an imaging device configured to acquire imaging data of a surgical site;
a surgical manipulator configured to hold a surgical tool; and
a controller connected to the imaging device and the surgical manipulator, wherein the controller is configured to receive the imaging data from the imaging device and derive, from the imaging data, trajectory for the surgical tool through an incision at the surgical site; wherein the controller is configured to derive the trajectory by deriving a set of distances indicative of an extent of displacement of a tip of the surgical tool along the trajectory; wherein the controller is configured to cause translation displacement of the surgical manipulator to translate the surgical tool along the trajectory; wherein the controller is configured to cause displacement of the surgical manipulator to move the tip of the surgical tool along the trajectory; wherein the controller is configured to derive the trajectory according to a parameterized model of the surgical site; wherein the controller is configured to derive the parametric model of the surgical site from the imaging data of the surgical site; wherein the imaging device includes a transpupillary imaging probe, and the controller is configured to derive the parameterized model of the surgical site from imaging data acquired by the transpupillary imaging probe; wherein the imaging device further includes an intraocular imaging probe, and the controller is configured to update the parameterized model of the surgical site from imaging date acquired by the intraocular imaging probe.

2. The surgical system of claim 1, wherein the controller is configured to derive the trajectory by performing a coordinate transformation between a reference frame of the imaging device and a reference frame of the surgical manipulator.

3. The surgical system of claim 1, wherein the controller is configured to derive the trajectory by deriving, from the imaging data, a set of insertion angles for the surgical tool through the incision.

4. The surgical system of claim 1, wherein the controller is configured to derive the trajectory such that a remote center of motion of the surgical tool is coincident with the incision.

5. The surgical system of claim 1, wherein the controller is configured to derive the trajectory by causing translational displacement of the imaging device relative to the incision.

6. The surgical system of claim 1, wherein the controller is configured to cause a speed of translation of the surgical tool to vary as a function of the extent of displacement of the tip of the surgical tool along the trajectory.

7. The surgical system of claim 1, wherein the parameterized model of the surgical site specifies a volume within which the trajectory is confined.

8. The surgical system of claim 1, wherein the parameterized model of the surgical site specifies a set of surfaces between which the trajectory is confined.

9. The surgical system of claim 1, wherein the controller is configured to identify a tissue adjacent to the tip of the surgical tool from the imaging data acquired by the intraocular imaging probe.

10. The surgical system of claim 1, wherein the controller is configured to derive a distance between the tip of the surgical tool and a tissue adjacent to the tip of the surgical tool from the imaging data acquired by the intraocular imaging probe.

11. The surgical system of claim 1, wherein the surgical tool is an aspiration tool, and the controller is configured to cause an aspiration force of the surgical tool to vary as a function of a position of the tip of the surgical tool along the trajectory.

12. The surgical system of claim 1, wherein the controller is configured to cause a rotation angle to vary about a centerline of the surgical tool as a function of a position of the tip of the surgical tool along the trajectory.

13. The surgical system of claim 1, wherein the imaging device includes an intraocular imaging probe, and the controller is configured to adjust functionality of the surgical tool according to imaging data acquired by the intraocular imaging probe.

14. The surgical system of claim 1, wherein the controller is configured to provide a user interface to visualize the surgical site for intraoperative monitoring and to provide an override function to adjust or terminate movement of the surgical tool along the trajectory.

15. The surgical system of claim 1, wherein the controller is configured to provide a user interface to visualize the surgical site for evaluation of surgical progress.

16. The surgical system of claim 15, wherein the user interface provides a function to select a following autonomous mode according to surgical progress.

17. The surgical system of claim 1, wherein the incision at the surgical site is configured to be scanned by the imaging device to derive an insertion trajectory.

18. The surgical system of claim 1, further wherein the trajectory is configured to be tracked to perform extraction of a lens.

19. The surgical system of claim 1, further wherein the imaging data from the imaging device is configured to update the model of the surgical site and adjust the trajectory.

* * * * *